US011648228B2

(12) United States Patent
Clarke et al.

(10) Patent No.: US 11,648,228 B2
(45) Date of Patent: May 16, 2023

(54) METHOD OF TREATMENT

(71) Applicant: TDeltaS Limited, Thame (GB)

(72) Inventors: Kieran Clarke, Oxford (GB); Brianna Stubbs, Oxford (GB)

(73) Assignee: TDELTAS LIMITED, Thame (GB)

( * ) Notice: Subject to any disclaimer, the term of this patent is extended or adjusted under 35 U.S.C. 154(b) by 84 days.

(21) Appl. No.: 16/651,255

(22) PCT Filed: Sep. 25, 2018

(86) PCT No.: PCT/GB2018/052717
§ 371 (c)(1),
(2) Date: Mar. 26, 2020

(87) PCT Pub. No.: WO2019/063984
PCT Pub. Date: Apr. 4, 2019

(65) Prior Publication Data
US 2020/0261392 A1 Aug. 20, 2020

(30) Foreign Application Priority Data
Sep. 27, 2017 (GB) .................................. 1715654

(51) Int. Cl.
A61K 31/22 (2006.01)
A61P 3/04 (2006.01)
A61K 31/70 (2006.01)
A61K 45/06 (2006.01)
A61K 9/00 (2006.01)

(52) U.S. Cl.
CPC .............. A61K 31/22 (2013.01); A61K 31/70 (2013.01); A61P 3/04 (2018.01); A61K 9/0095 (2013.01); A61K 45/06 (2013.01); A61K 2800/92 (2013.01)

(58) Field of Classification Search
CPC ............ A61K 31/22; A61K 31/70; A61P 3/04
See application file for complete search history.

(56) References Cited

U.S. PATENT DOCUMENTS

| 6,323,237 | B1 | 11/2001 | Veech |
| 6,380,244 | B2 † | 4/2002 | Martin |
| 7,807,718 | B2 † | 10/2010 | Hashim |
| 8,642,654 | B2 * | 2/2014 | Clarke .................... A61P 21/00 560/179 |
| 9,925,164 | B1 † | 3/2018 | Hashim |
| 2006/0280721 | A1 | 12/2006 | Veech et al. |
| 2007/0208081 | A1 | 9/2007 | Gross |
| 2007/0286916 | A1 | 12/2007 | Bengmark |
| 2009/0253781 | A1 | 10/2009 | Veech |
| 2011/0237666 | A1 | 9/2011 | Clarke et al. |
| 2012/0322719 | A1 | 12/2012 | Pavlov |
| 2015/0164855 | A1 | 6/2015 | Clarke |
| 2015/0283163 | A1 | 10/2015 | Rayburn et al. |
| 2016/0108442 | A1 | 4/2016 | Adelstein et al. |
| 2016/0263098 | A1 | 9/2016 | Mantzoros |
| 2017/0296501 | A1 | 10/2017 | Lowery |
| 2018/0008629 | A1 | 1/2018 | Dixit |
| 2019/0117612 | A1 † | 8/2019 | Hashim |

FOREIGN PATENT DOCUMENTS

| CN | 102164884 A | 8/2011 |
| GB | 2517088 A | 2/2015 |
| WO | WO2004108740 A2 | 12/2004 |
| WO | WO2006020137 A2 | 2/2006 |
| WO | WO2006020179 A1 | 2/2006 |
| WO | WO2008110034 A1 | 9/2008 |
| WO | WO2009089144 A1 | 7/2009 |
| WO | WO2010021766 A1 | 2/2010 |
| WO | WO2014140308 A1 | 9/2014 |
| WO | WO2014153416 A1 | 9/2014 |
| WO | WO2014190251 A1 | 11/2014 |
| WO | WO2016123229 A1 | 8/2016 |
| WO | WO2017184788 A1 | 10/2017 |
| WO | WO2019002828 A1 | 1/2019 |

OTHER PUBLICATIONS

Examination Report for Corresponding European Application No. 18 737 388.1, dated Oct. 26, 2021, 4 pages.
International Search Report of corresponding PCT/GB2019/052797, dated Jan. 3, 2020, 4 pages.
Cox et al., "Nutritional Ketosis Alters Fuel Preference and Thereby Endurance Performance in Athletes", Cell Metabolism, Cell Press, vol. 24, No. 2, Jul. 27, 2016, p. 256-268, XP029680184.
Henderson et al. (http://patient.info/doctor/steatohepatitis-and-steatosis-fatty-liver (last Edited Aug. 31, 2016)) (Year: 2016).
Holdsworth et al., "A Ketone Ester Drink Increases Postexercise Muscle Glycogen Synthesis in Humans", Medicine and Science in Sports and Exercise, vol. 49, No. 9, Sep. 1, 2017, p. 1789-1795, XP055649184.
Kreher et al., "Overtraining Syndrome: a Practical Guide", Sports Health: a Multidisciplinary Approach, vol. 4, No. 2, Jan. 31, 2012, p. 128-138, XP055649498.
Parker et al., "Beta-hydroxybutyrate favorably alters muscle cell survival and mitochondrial bioenergetics", Apr. 1, 2017, Retrieved from the Internet: URL:https://www.fasebj.org/doi/abs/10.1096/fasebj.31.1_supplement.883.7, XP055649476.

(Continued)

Primary Examiner — Kevin E Weddington
(74) Attorney, Agent, or Firm — Lewis Roca Rothgerber Christie LLP

(57) ABSTRACT

The present invention provides a method of suppressing hunger by lowering plasma ghrelin levels comprising administration of a compound to a human or animal body, wherein the compound is selected from: (i) (R)-3-hydroxybutyrate; (ii) an ester of (R)-3-hydroxybutyrate; and (iii) an oligomer of (R)-3-hydroxybutyrate moieties; or a pharmaceutically acceptable salt or solvate thereof. The invention also provides a method of administering such a compound in a dosage effective to reduce hunger in order that a cosmetically beneficial loss or maintenance of body weight occurs, wherein in the method, plasma ghrelin levels are lowered. The aforementioned compound is also provided for use in a method of treatment of the human or animal body wherein the compound is administered and hunger is suppressed by lowering of plasma ghrelin levels. The compound is particularly useful for subjects having conditions associated with overeating, such as overweight, obese, severely obese patients or diabetic patients.

30 Claims, 7 Drawing Sheets

(56) References Cited

OTHER PUBLICATIONS

Thomsen et al., "Effects of 3-hydroxybutyrate and free fatty acids on muscle protein kinetics and signaling during LPS-induced inflammation in humans: anticatabolic impact of ketone bodies", The American Journal of Clinical Nutrition, vol. 108, No. 4, Oct. 1, 2018, p. 857-867, XP055649308.

UK Patent Office action issued dated Jan. 27, 2021, issued in GB Patent Application No. 1815588.7, 5 pages.

Szczepaniak, et al., "Magnetic Resonance Spectroscopy to Measure Hepatic Triglyceride Content: Prevalence of Hepatic Steatosis in the General Population", Am J Physiol Endocrinol Metab, 288:E462-E468, 2005.

Fracanzani, et al., "Risk of Nonalcoholic Steatohepatitis and Fibrosis in Patients with Nonalcoholic Fatty Liver Disease and Low Visceral Adiposity", Author Manuscript, available at http://hdl.handle.net/2318/83956, 24 pp. (subsequently published at Journal of Hepatology, vol. 54, Issue 6, 2011) doi:10.1016/j.jhep.2010.09.037.

Das, et al., "Nonobese Population in a Developing Country Has a High Prevalence of Nonalcoholic Fatty Liver and Significant Liver Disease", Hepatology, 2010:1593-1602.

Kemper, et al., "An Ester of B-Hydroxybutyrate Regulates Cholesterol Biosynthesis in Rats and a Cholesterol Biomarker in Humans", Lipids (2015) 50:1185-1193.

Unknown, "Keto forum: the Best Fatty Liver Diet", 18 pages, downloaded Aug. 15, 2018 from https://www.ruled.me/keto-best-fatty-liver-diet.

Machado, et al., "No Need for a Large Belly to Have NASH", Journal of Hepatology, 2011, 54:1090-1093.

Margariti, et al., "Non-alcoholic Fatty Liver Disease May Develop in Individuals with Normal Body Mass Index", Annals of Gastroenterology (2012) 25:45-51.

Pavlides, et al., "Multiparametric Magenetic Resonance Imaging Predicts Clinical Outcomes in Patients with Chronic Liver Disease", Journal of Hepatology, 2016, 64:308-315.

Pawlak, et al., "Ketone Body Therapy Protects from Lipotoxicity and Acute Liver Failure Upon Ppara Deficiency", Mol Endocrinol, 2015, 29(8):1134-1143.

Thomas, et al., "Hepatic Triglyceride Content and its Relation to Body Adiposity: a Magnetic Resonance Imaging and Proton Magnetic Resonance Spectroscopy Study", Gut, 2005, 54:122-127.

Jacobs et al, "Creatine Supplementation may prevent NAFLD by stimulating fatty acid oxidation", & Join I Annual Meeting of the ASPET/BPS at Experimental Biology (EB); Boston, MA, USA; Apr. 20-24, 2013 vol. 27, Apr. 1, 2013 (Apr. 1, 2013), FASEB Journal, Abstract only. Retrieved from the Internet: URL:https://www.fasebj.org/doi/abs/10.1096/fasebj.27.1_supplement.222.2.

International Search Report and Written Opinion of corresponding PCT/GB2018/051752, dated Oct. 17, 2018, 14 pages.

Gibson et al., "Do ketogenic diets really suppress appetite? A systematic review and meta-analysis", Obesity Reviews, 16:64-76 (2015).

Sumithran et al., "Ketosis and appetite-mediating nutrients and hormones after weight loss", European Journal of Clinical Nutrition (2013) 67:759-764.

Johnstone et al., "Effects of a high-protein ketogenic diet on hunger, appetite and weigh loss in obese men feeding ad libitum", Am J Clin Nutr, 87:44-55 (2008).

Paoli et al., "Ketosis, ketogenic diet and food intake control: a complex relationship", Frontiers in Psychology, vol. 6, Article 17, pp. 1-9, 2015.

Chearskul et al., "Effect of weight loss and ketosis on postprandial cholecystokinin and free fatty acid concentrations", Am J Clin Nutr,2008:87:1238-46.

Clarke et al., "Kinetics, safety and tolerability of (R)-3-hydroxybutyl (R)-3-hydroxybutyrate in healthy adult subjects", Regulatory Toxicology and Pharmacology, 63:401-408 (2012).

Chacko et al., "Effect of ghrelin on glucose regulation in mice", Am J Physiol Endocrinol Metab 302: E1055-E1062, 2012.

Stubbs et al., "A ketone ester drink lowers human ghrelin and appetite", Obesity, vol. 26, No. 2, 2018, pp. 29-273.

Pawan et al., "Effects of 3-hydroxybutyrate on obese subjects on very-low-energy diets", The Lancet, Jan. 1983, Elsevier, vol. 321, pp. 15-17.

Srivastava et al., "Mitochondroial biogensis and increased uncoupling protein 1 in brown adipose tissue of mice fed a ketone ester diet", The FASEB Journal; vol. 26, No. 6, 2012, pp. 2351-2362.

Rossi et al., "Suppression of feed intake after parenteral administration of D-B-hydroxybutyrate in pygmy goats", Journal of Veterinary Medicine A, vol. 47, No. 1, 2000, pp. 9-16.

GB Search Report dated May 22, 2018 issued in GB Application No. GB1715654.8.

GB Search Report dated Mar. 21, 2019, issued in GB Application No. GB1815588.7.

Frayne, "Metabolic Regulation a Human Perspective", 2d Edition, 2003, pp. 94-96.

International Preliminary Report on Patentability dated Mar. 31, 2020, issued in PCT/GB2018/052717, 9 pages.

Wade, A and Weller, PJ, "Handbook of Pharmaceutical Excipients, 2d Edition" 1994.

Walker, Abigail, et al., "Anosmia and loss of smell in the era of covid-19," BMJ 2020;370:m2808 http://dx.doi.org/10.1136/bmj.m2808, published Jul. 21, 2020, 4 pages.

Chinese Office action for corresponding Chinese Application No. CN 201880062296.6, dated Aug. 1, 2022, 9 pages and English translation, 16 pages.

\* cited by examiner
† cited by third party

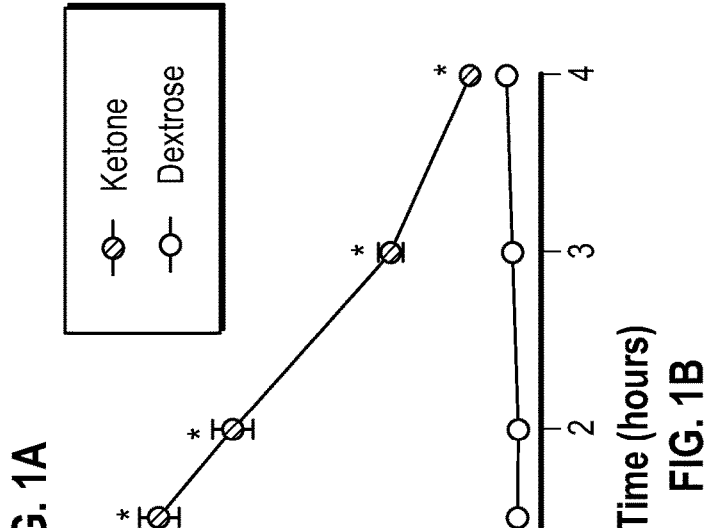
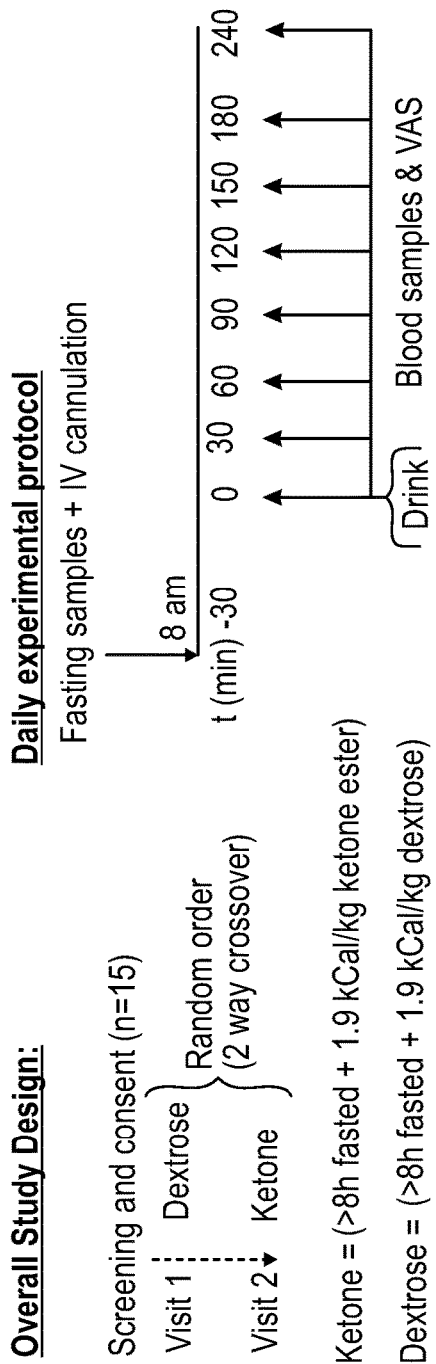
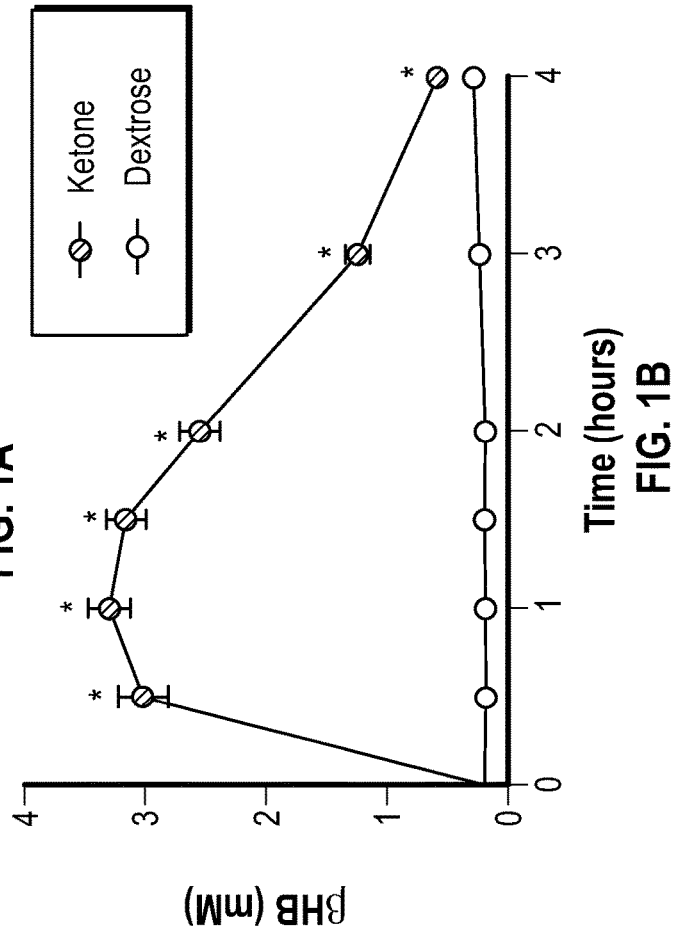
FIG. 1A
FIG. 1B

METHOD OF TREATMENT

CROSS-REFERENCE TO RELATED APPLICATION(S)

This application is a National Phase Patent Application and claims priority to and the benefit of International Application Number PCT/GB2018/052717, filed on Sep. 25, 2018, which claims priority to British Patent Application Number 1715654.8, filed on Sep. 27, 2017, the entire contents of all of which are incorporated herein by reference.

FIELD OF THE INVENTION

The present invention relates to methods and compounds for use in suppressing hunger in a subject and to treatments of conditions, such as obesity, by modifying ghrelin levels. The invention also relates to prophylactic treatment of a subject to avoid, or reduce, the risk of developing conditions associated with overeating, such as obesity and diabetes.

BACKGROUND OF THE INVENTION

Over-eating can lead to excess body weight. In some cases, over-eating can lead to obesity, which is associated, in turn, with conditions such as pre-diabetes, diabetes, metabolic syndrome, high blood pressure, heart attacks, heart failure and stroke. Public health may be improved by reducing excess body weight to normal levels in subjects having excess body weight, whether or not they are healthy or have a disease associated with excess body weight.

In cases where the amount of excess body weight of a subject is not so large as to endanger their health, excess body weight may nonetheless be of concern. It may be desirable to minimize excess body weight for the purposes of appearance. Whether or not a subject's health is at risk due to excess body weight, it may be advantageous to avoid further weight gain or to enable weight loss by reducing or preventing over-eating.

In healthy subjects with little or no excess body weight, it is also prudent to avoid the accumulation of excess body-weight by reducing or preventing over-eating.

One approach to prevention of over-eating is the modulation of hunger. It is known that diets that are 'ketogenic' (low-carbohydrate, high-fat) are an effective strategy for weight-loss and have been experimentally and anecdotally linked to decreased appetite (Gibson et al., "Do ketogenic diets really suppress appetite? A systematic review and meta-analysis", Obes Rev. 2015, 16(1):64-76; Sumithran et al., "Ketosis and appetite-mediating nutrients and hormones after weight loss", Eur J Olin Nutr. 2013, 67(7):759-64; Johnstone et al., "Effects of a high-protein ketogenic diet on hunger, appetite, and weight loss in obese men feeding ad libitum", Am J Clin Nutr. 2008, 87(1):44-55). During a high-fat, low-carbohydrate (ketogenic) diet, the human or animal body produces ketones in the liver from fatty acids released from adipose tissue. Ketones are then oxidised by the brain as an alternative energy source to glucose, when falling blood glucose levels threaten cerebral function.

The precise effects of a ketogenic diet on the body are not fully understood. In particular, the mechanism by which ketogenic diets can decrease hunger, and thereby reduce calorie intake, is not clear (Gibson et al. and Sumithran et al., cited above). Decreased hunger during a ketogenic diet may be linked to elevated plasma ketone levels. It has been postulated that one possible mechanism whereby ketones could decrease hunger is via central actions in the brain; another possibility is by changes to peripheral hormone secretion (Paoli et al., "Ketosis, ketogenic diet and food intake control: a complex relationship", Front Psychol., 2015, 6:27).

An effect observed in patients following a ketogenic diet is alteration of fasting and post-meal levels of some gut hormones, including the 'hunger-hormone,' ghrelin (Sumithran et al., cited above; Chearskul et al., "Effect of weight loss and ketosis on postprandial cholecystokinin and free fatty acid concentrations", Am J Clin Nutr. 2008, 87(5): 1238-46). Ghrelin, produced by oxyntic cells of the stomach, is highest in the plasma during periods of starvation and is rapidly down-regulated following a meal. Ghrelin acts on the hypothalamus and vagus nerve to stimulate feeding. Basal circulating plasma ghrelin levels are raised following periods of restricted food intake and weight-loss. Increased basal ghrelin is implicated in over-eating and weight-regain following a diet.

However, the connection between a ketogenic diet, ghrelin levels and weight loss is unclear. A ketogenic diet is high in fat and low in carbohydrates, the fat content of the diet affecting the level of ketosis in the body. Further, the fat content of the diet can affect a dieter's ability to lose weight. In some studies, it has been found that a ketogenic diet may not lead to weight loss: for instance, it has been shown that diets low in fat resulted in greater body fat loss compared to a carbohydrate restricted diet (such as in a typical ketogenic diet), highlighting that metabolic changes during caloric restriction are complex.

Accordingly, there is a need for a new and effective method for decreasing hunger and for enabling weight loss or maintenance of a healthy weight without relying on a ketogenic diet.

The effects of exogenous ketone ester on the human and animal body have been investigated. Consumption of an exogenous ketone ester can raise levels of blood plasma (R)-3-hydroxybutyrate, also referred to as D-β-hydroxybutyrate or BHB (Clarke et al., "Kinetics, safety and tolerability of (R)-3-hydroxybutyl (R)-3-hydroxybutyrate in healthy adult subjects", Regul Toxicol Pharmacol., 2012, 63(3):401-8).

In U.S. Pat. No. 8,642,654 it was shown that one particular enantiomer of the ketone ester, (R)-3-hydroxybutyl (R)-3-hydroxybutyrate, could be consumed and was converted to (R)-3-hydroxybutyrate in the body.

It is generally understood that the term "ketone bodies" encompasses three compounds: (R)-3-hydroxybutyrate, acetoacetate and acetone. Ketone bodies are produced by the liver from fatty acids during periods of low food intake.

In U.S. Pat. No. 8,642,654 (corresponding also to WO2010/021766), BHB was shown to reduce plasma levels of fatty acids and was therefore implicated in conditions associated with high plasma levels of fatty acids and suggested for uses including weight loss, improvements of cognitive function, alertness, reducing neurodegeneration, free radical toxicity, hypoxic conditions and hyperglycaemia. The ketone ester 3-hydroxybutyl 3-hydroxybutyrate was found to suppress appetite in rats, as well as improve cognitive function and inhibit neurodegeneration in mice. However, the hormone ghrelin was not investigated.

In WO2014/190251 a method for suppressing appetite is disclosed, comprising administering an effective amount of bioderived (R)-3-hydroxybutyl (R)-3-hydroxybutyrate.

WO2017/184788 discloses the administration of BHB directly to a subject, and mentions also the use of ketone esters. A variety of uses for these compounds are mentioned, including appetite suppression.

WO2014/153416 discloses the administration of BHB salts to a subject, leading to ketosis and the reduction of hunger.

None of the above mentioned prior art documents disclose the use of exogenous ketone esters for the suppression of hunger by lowering plasma ghrelin levels.

Ketone bodies and ketone body esters have also been shown to have various other uses, such as treatment of muscle impairment or fatigue, and protection from radiation exposure. However, these compounds have not been shown to have an effect on gut hormone levels.

It has now been surprisingly found that administration of a ketone ester to a subject can produce the advantageous effect of the ketogenic diet: specifically, suppression of the hunger hormone ghrelin and hence the suppression of hunger, without the disadvantages typically associated with the ketogenic diet (particular disadvantages include the difficulty of ensuring compliance with a diet, the potential for weight gain by increasing the fat content of the diet and the potential loss of nutrients, such as vitamins, due to a restricted diet). As detailed above, the mechanism by which ketogenic diets can decrease hunger and reduce calorie intake is not clear. Ketogenic diets result in numerous biochemical effects within the body to which a reduced hunger could be attributed. There is no teaching in the prior art that the consumption of exogenous ketones can influence ghrelin levels.

A ketone ester may be administered to a subject according to the method of the invention, whether the subject has excess body weight or not, and so the method may be used to prevent weight gain (in both healthy and overweight subjects) as well as to promote weight loss in overweight subjects. The methods and compounds of the invention may be used in conjunction with a normal diet, so are suitable for subjects who are unwilling, or unable, to follow a ketogenic diet. The invention therefore offers significant advantages for public health.

SUMMARY OF THE INVENTION

The present invention therefore provides, in a first aspect, a method of suppressing hunger in a human or animal subject by lowering plasma ghrelin levels in the subject, comprising administration of a compound to the human or animal subject, wherein the compound is selected from:
(i) (R)-3-hydroxybutyrate;
(ii) an ester of (R)-3-hydroxybutyrate; and
(iii) an oligomer of (R)-3-hydroxybutyrate moieties;
or a pharmaceutically acceptable salt or solvate thereof.

Also provided, in a second aspect of the invention, is a method of improving the bodily appearance of a human or animal subject, which comprises administering to said human or animal subject a compound selected from:
(i) (R)-3-hydroxybutyrate;
(ii) an ester of (R)-3-hydroxybutyrate; and
(iii) an oligomer of (R)-3-hydroxybutyrate moieties;
or a salt or solvate thereof; in an amount effective to reduce hunger by lowering plasma ghrelin levels in order that a cosmetically beneficial loss or maintenance of body weight occurs.

In a third aspect of the invention there is provided a compound selected from:
(i) (R)-3-hydroxybutyrate;
(ii) an ester of (R)-3-hydroxybutyrate; and
(iii) an oligomer of (R)-3-hydroxybutyrate moieties;
or a pharmaceutically acceptable salt or solvate thereof; for use in a method of treatment of a human or animal subject wherein the compound is administered and hunger is suppressed by lowering of plasma ghrelin levels.

In a fourth aspect of the invention there is provided a pharmaceutically composition for use in a method of treatment of a human or animal subject, wherein the composition is administered and hunger is suppressed by lowering of plasma ghrelin levels, comprising a compound selected from:
(i) (R)-3-hydroxybutyrate;
(ii) an ester of (R)-3-hydroxybutyrate; and
(iii) an oligomer of (R)-3-hydroxybutyrate moieties;
or a pharmaceutically acceptable salt or solvate thereof, and one or more pharmaceutically acceptable excipients.

In a fifth aspect of the invention there is provided the use of a compound selected from:
(i) (R)-3-hydroxybutyrate;
(ii) an ester of (R)-3-hydroxybutyrate; and
(iii) an oligomer of (R)-3-hydroxybutyrate moieties;
or a pharmaceutically acceptable salt or solvate thereof, or the use of a composition comprising a compound selected from:
(i) (R)-3-hydroxybutyrate;
(ii) an ester of (R)-3-hydroxybutyrate; and
(iii) an oligomer of (R)-3-hydroxybutyrate moieties;
or a pharmaceutically acceptable salt or solvate thereof, and one or more pharmaceutically acceptable excipients, in the manufacture of a medicament for use in a method of treatment of a human or animal subject wherein, in the method, the compound or composition is administered and hunger is suppressed by lowering of plasma ghrelin levels.

In this invention, plasma ghrelin levels are lowered with respect to the levels immediately before administration of the compound to the human or animal body. A wide variety of factors are involved in appetite and hunger suppression, as detailed above. The inventors found that compounds according to the invention can be administered and reduce hunger specifically via acting on levels of the ghrelin hormone. Modification of ghrelin levels in this manner is easily reversible and directly leads to reduced hunger and food intake, thereby avoiding the side-effects of a typical ketogenic diet.

BRIEF DESCRIPTION OF THE FIGURES

FIG. 1 shows the experimental design, the study protocol and the blood D-$\beta$HB (i.e. $\beta$HB) concentrations in 15 human subjects for 4 hours after drinking either a ketone drink or an isocaloric dextrose drink. The asterisks mark the significantly higher blood $\beta$HB concentrations following the ketone drink. The values are means±SEM (standard error of the mean).

DETAILED DESCRIPTION OF THE INVENTION

Figure 2A:
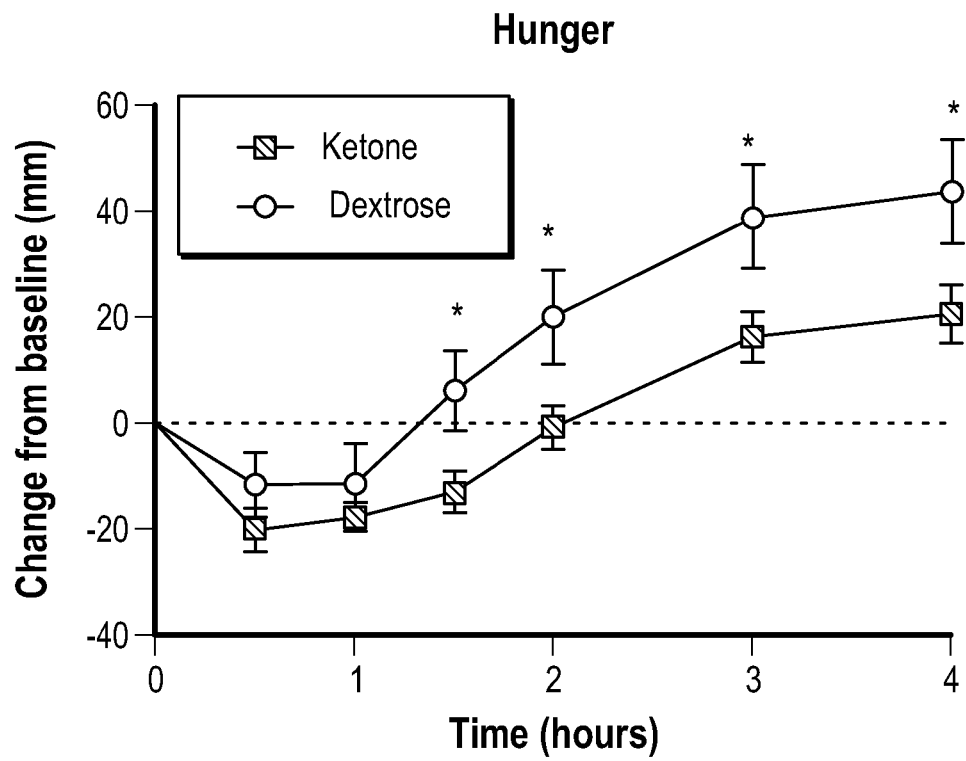
FIG. 2A-C shows the changes from baseline in visual analogue scale responses for Hunger, Desire to eat and Fullness in 15 human subjects for 4 hours after drinking either a ketone drink or an isocaloric dextrose drink.
Figure 2B:
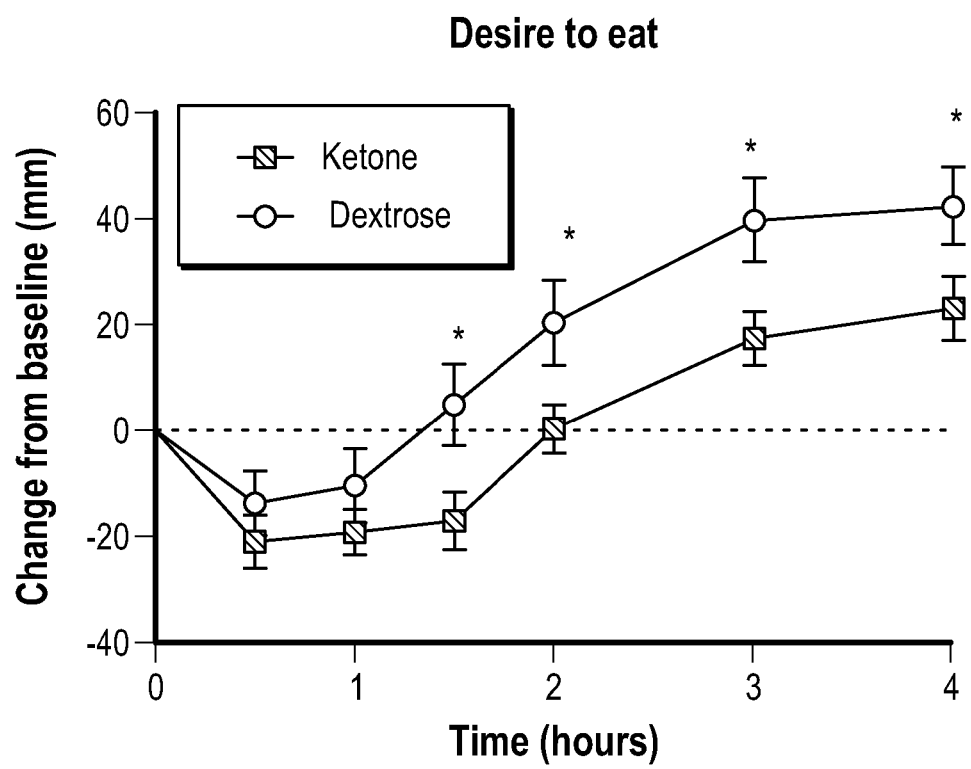

The method of the invention concerns the administration of (R)-3-hydroxybutyrate or a precursor thereof in order to suppress hunger wherein, as a result of the administration, hunger is suppressed via lowering of plasma ghrelin levels.

By "administration" is meant the delivery of the compound to the human or animal body, i.e. to the "subject" of the invention Typically, the compound will be ingested or consumed by the human or animal body, i.e. administered orally. Other modes of administration are also included within the scope of this invention—for instance delivery of the compound by intravenous injection or nasogastric tube.

The suppression of hunger can prevent a subject from gaining weight, or ensure that a subject's body weight is maintained (that is, does not increase). The suppression of hunger generally leads to the subject eating less. Thus, the method of the invention usually involves lowering or maintaining the body weight of a subject. Typically, therefore, the method comprises administration of a compound according to the third aspect of the invention, or an acceptable salt or solvate thereof, in a dosage effective to ensure that a loss or maintenance of body weight occurs by reducing hunger and lowering plasma ghrelin levels.

According to the invention, the body weight of a subject may be maintained (that is, prevented from increasing) or reduced. By "body weight" is typically meant "body fat content", and accordingly, in a preferred embodiment, the invention leads to a reduction in the body fat of a subject.

In one embodiment, the method of the invention is a method of treatment of the human or animal body. For instance, where a subject is overweight (e.g. the subject has a body mass index of 25 or higher), reducing hunger with the consequence of reducing or preventing any increase of body weight is typically beneficial to the health of that subject. Accordingly, the method of the invention may often be regarded as a method of medical treatment where the subject is overweight (i.e. has a body weight greater than the maximum healthy weight for the subject) and the treatment is beneficial to the health of the subject.

In another embodiment, the method of the invention is performed for cosmetic purposes, to improve the bodily appearance of a human or animal. The method of the invention may accordingly be non-therapeutic. For instance, where a subject is not overweight (e.g. the subject has a body mass index of less than 25), reducing body weight or preventing any increase in body weight may not have obvious health benefits for the subject. Accordingly, the method of the invention may be regarded as a cosmetic method where the beneficial effects of hunger suppression improve the subject's appearance.

The methods and compounds for use according to the invention lower plasma ghrelin levels. By "plasma ghrelin levels" is meant the level of ghrelin in the blood plasma of a subject. By "lowered" is meant that the plasma ghrelin levels are lower than their value shortly before (e.g. 1 minute or less before) the time at which the compound is administered.

The subject of the invention may ingest a meal during the methods disclosed herein. Ingesting a meal generally lowers plasma ghrelin levels, but administration of a compound according to this invention potentiates and prolongs this effect. In the methods of the invention, plasma ghrelin levels are typically lowered rapidly following a meal to and remain significantly lower for between 1 and at least 4 hours after administration of a compound of the invention.

The plasma ghrelin level of the subject usually stays at a lower level than the initial level (i.e. the level at the time of administration of a compound of the invention) for at least one or two hours, preferably for at least three hours or up to five hours. These values assume that the subject is at rest and does not eat during the interval in question.

Usually, in the methods of the invention, plasma ghrelin levels are lowered by ~180 pg/ml, from a baseline of ~500 pg/ml, following the consumption of food. That is, the plasma ghrelin level of the subject falls by ~180 pg/ml compared to the plasma ghrelin level of the subject shortly before (e.g. 1 minute before) food. Following administration of (R)-3-hydroxybutyrate and the precursors thereof described herein, plasma ghrelin remains ~100 pg/ml below baseline for 1-3 hours, and ~100 pg/ml below the levels observed following other foods for 1 to 4 hours. In some embodiments of the methods of the invention, plasma ghrelin levels are 100 pg/ml or lower than baseline or following consumption of other foods.

Usually, the subject's plasma ghrelin level shortly before (e.g. 1 minute before) consumption of food is between 400 and 600 pg/ml. Food lowers the subject's plasma ghrelin level to around 320 pg/ml. In the methods of the invention, following ketone administration, ghrelin levels remain at ~320 pg/ml for at least 1 to 3 hours.

Typically, the subject's plasma ghrelin levels remain lower than the plasma ghrelin level of the subject shortly before (e.g. 1 minute before) administration of said compounds for up to five hours following administration of the compound. Of course, this period includes an initiation period (typically up to an hour, for example up to 30 minutes) during which the subject's plasma ghrelin levels are lowered by at least 180 pg/ml. For example, the subject's plasma ghrelin level remains at a level at least 50 pg/ml or at least 100 pg/ml lower than the plasma ghrelin level shortly before administration during the period from 1 to 4 hours (e.g. from 2 to 3 hours) after administration.

Thus, in some embodiments of the methods of the invention the subject's plasma ghrelin levels are maintained at 500 pg/ml or less, preferably 400 pg/ml or 300 pg/ml or less, during the period from 1 to 4 hours (e.g. from 2 to 3 hours) after administration.

In particularly advantageous embodiments of the methods of the invention, the subject's plasma ghrelin levels are lowered by at least 180 pg/ml compared to the level shortly before administration, and are maintained at a value a value at least 180 pg/ml below the level shortly before consumption for 2 to 4 hours after administration.

In some embodiments of the invention, the methods and compounds of the invention suppress a subject's hunger at a mealtime and hence reduce the risk of over-eating during a meal. Thus, in some embodiments of the invention, the compound of the invention is administered up to five hours before a meal. The compound of the invention may be administered at least 1 hour before a meal, or at least 30 minutes before a meal.

The compounds of the invention act rapidly and accordingly in some embodiments the compound of the invention may be administered immediately before a meal. In such embodiments, the compound is administered typically from 0 to 30 minutes before a meal, e.g. up to 15 minutes before a meal. Typically, the compound of the invention is administered from 0 minutes up to 5 hours before a meal, preferably from 5 minutes up to 2 hours before a meal (e.g. from 30 minutes to 1 hour before a meal). The compound may alternatively be administered at the start of the meal.

In some embodiments of the invention, the methods and compound of the invention suppress a subject's hunger between mealtimes and hence reduce the risk of eating unnecessarily after meals or between meals. Advantageously, the compounds of the invention suppress plasma ghrelin levels for significant periods of time and so can be used to reduce hunger and reduce the risk of over-eating for the entire morning (between breakfast and lunch), or the entire afternoon (between lunch and dinner) or the entire night (between dinner and breakfast). The compound acts rapidly to reduce plasma ghrelin levels and so, if administered after a meal, it can suppress hunger immediately with an effect lasting until the next meal.

Thus, in some embodiments of the invention the compound of the invention is administered immediately after a meal. The compound of the invention may be administered up to 2 hours after a meal, or up to 1 hour (e.g. up to 30 minutes) after a meal. In some embodiments, the compound of the invention may be administered with a meal.

As plasma ghrelin levels are typically lowered after eating, there may be reduced need to suppress hunger immediately after a meal and so to prolong the time during which hunger is suppressed, the compound of the invention may be administered a short period after a meal. For instance, the compound of the invention may be administered from 15 minutes and up to 3 hours after a meal, preferably from 30 minutes up to 2 hours (e.g. from 1 to 2 hours) after a meal.

(R)-3-hydroxybutyrate and the precursors thereof described herein are referred to as the compounds of the invention. The invention provides such compounds for use in a method of medical treatment, and also provides methods of hunger suppression, methods of medical treatment and cosmetic methods using such compounds.

The compounds of the invention provide a source of (R)-3-hydroxybutyrate in the body of the subject. Accordingly, the compound may be (R)-3-hydroxybutyrate itself, or a precursor to (R)-3-hydroxybutyrate, such as an ester or oligomer thereof, which can be broken down in the body to form (R)-3-hydroxybutyrate.

(R)-3-hydroxybutyrate is a ketone body, as defined in "Metabolic Regulation: A Human Perspective" by K N Frayn. WO2004/108740 discloses that a ketone body ester may be consumed by rats to achieve elevated levels of ketone bodies. The manufacture of ketone esters has been disclosed, for instance, in WO2014/140308, which describes processes for producing (R)-3-hydroxybutyl (R)-3-hydroxybutyrate.

An ester of (R)-3-hydroxybutyrate can be produced via a transesterification reaction of ethyl-(R)-3-hydroxybutyrate with an alcohol. This reaction may be enzyme catalysed. For instance, an ethyl ester of (R)-3-hydroxybutyrate and (R)-1,3-butanediol may be reacted together in the presence of immobilized lipase using a mild vacuum to remove the resultant ethanol by-product.

In a preferred embodiment of the invention, the ester of (R)-3 hydroxybutyrate is a compound of general formula I:

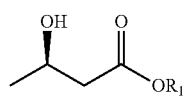

I wherein:

$R_1$ is a $C_1$-$C_6$ alkyl group, which alkyl group carries up to five —$OR_2$ substituents, $R_2$ represents hydrogen, or $C_1$-$C_6$ alkyl or —$OR_2$ represents a (R)-3-hydroxybutyrate moiety; or $R_1$ is a moiety derived from an alcohol $HOR_1$, wherein said alcohol is a sugar.

Typically, zero, one or two —$OR_2$ groups represent a (R)-3-hydroxybutyrate moiety. Preferably, only zero or one —$OR_2$ groups represent a (R)-3-hydroxybutyrate moiety.

Preferred compounds of the invention are esters, particularly those as outlined in formula I above. The $R_1$ moiety is derived from a corresponding alcohol HO—$R_1$. Alcohol HO—$R_1$ may be, for instance, a mono-alcohol, a di-ol, a polyol, or a sugar.

Preferably, in formula I, $R_1$ is a $C_1$-$C_6$ alkyl group substituted with 0, 1, 2, 3, 4 or 5 —$OR_2$ substituents. Most preferably, $R_1$ is a $C_1$-$C_6$ alkyl group substituted with 1, 2 or 3 —$OR_2$ substituents, typically 1 or 2 —$OR_2$ substituents.

Preferably, $R_2$ is H.

Preferably, $R_1$ has formula —$CH_2$—CH(OH)—$CH_2$(OH) or —$CH_2$—$CH_2$—CH(OH)—$CH_3$. In these cases, $R_1$ is a moiety derived from an alcohol HO—$R_1$ which corresponds to butanediol and glycerol, respectively. The butanediol may be racemic 1,3 butanediol. Most preferably, the alcohol HO—$R_1$ corresponds to R-1,3 butanediol. In this case the group $R_1$ is of formula:

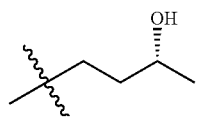 [SMILES: *CC[C@@H](C)O]

Preferably, the compound of the invention is a monoester, i.e. in cases where the alcohol HO—$R_1$ comprises more than one pendant hydroxyl, only one of these reacts to form a hydroxybutyrate moiety. Partial esters are compounds wherein the alcohol HO—$R_1$ comprises more than one pendant hydroxyl, and not all of these have reacted to form a hydroxybutyrate moiety.

A particularly preferred compound of the invention is (R)-3-hydroxybutyrate (R)-1,3-butanediol monoester of formula:

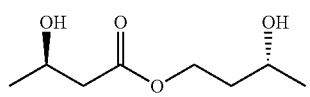

A further preferred compound of the invention is (R)-3-hydroxybutyrate-glycerol partial ester, i.e. (R)-3-hydroxybutyrate-glycerol monoester or diester.

In a different embodiment of the invention, $R_1$ is derived from an alcohol $HOR_1$, wherein said alcohol is a sugar. The sugar may be selected from altrose, arabinose, dextrose, erythrose, fructose, galactose, glucose, gulose, idose, lactose, lyxose, mannose, ribose, ribulose, sucrose, talose, threose, and xylose.

In cases where $R_1$ is derived from an alcohol $HOR_1$ which is a polyol, the polyol may be selected from glycerol, ribitol and xylitol.

In an alternative embodiment of the invention, the compound of the invention is of formula:

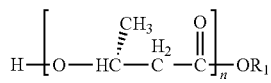

wherein:
R₁ is as defined above; and
n is an integer of from 2 to 100.

Preferably, n is from 2 to 50, for instance, 2 to 20, 2 to 10, 4 to 10 or 2 to 5. The oligomer may for instance comprise just 2, 3, 4 or 5 repeating units (n=2, 3, 4 or 5). The oligomer may be linear or cyclic in nature.

In a preferred embodiment of the invention, R₁ has formula —CH₂—CH(OH)—CH₂(OH) or —CH₂—CH₂—CH(OH)—CH₃, i.e. the alcohol used to form the ester is glycerol or 1,3 butanediol. The butanediol may be racemic 1,3 butanediol or (R)-1,3 butanediol. Preferably, it is (R)-1,3 butanediol.

When the compounds of the invention contain a chiral centre in addition to that depicted in the formulae above, the compounds may be present as racemic mixtures or pure enantiomeric forms.

Compounds of the invention may be present as pharmaceutically or physiologically compatible salts. For instance, sodium, potassium, calcium or magnesium salts thereof, may be employed.

Preferred compounds of the invention are present as sodium and/or potassium salts of (R)-3-hydroxybutyrate. The compounds may be present as mixed sodium/potassium salts of (R)-3-hydroxybutyrate.

Other preferred compounds of the invention are glycerol esters of (R)-3-hydroxybutyrate.

We have found that (R)-3-hydroxybutyrate-R-1,3-butanediol monoester and (R)-3-hydroxybutyrate-glycerol partial esters provide high circulating levels of (R)-3-hydroxybutyrate in the blood and reduce plasma ghrelin levels. Furthermore, these esters provide a surprisingly high level of uptake in the gut, thereby enabling high blood concentrations of (R)-3-hydroxybutyrate to be achieved upon consumption of a drink.

Accordingly, in a preferred embodiment, the invention provides a method of suppressing hunger according to the first aspect of the invention, or a method of improving appearance according to the second aspect of the invention, comprising administering a hydroxybutyrate ester or partial ester, for example (R)-3-hydroxybutyrate butane-1,3-diol monoester and (R)-3-hydroxybutyrate glycerol partial ester to a subject. In another preferred embodiment, the invention provides a hydroxybutyrate ester or partial ester, for example (R)-3-hydroxybutyrate butane-1,3-diol monoester and (R)-3-hydroxybutyrate glycerol partial ester for use according to the third aspect of the invention.

Particularly advantageous is (R)-3-hydroxybutyl-(R)-3-hydroxybutyrate as it allows a large rise in blood (R)-3-hydroxybutyrate to be achieved with oral ingestion of a smaller volume of material than with racemic ketones. A subject ingesting the material prior to, or during physical exercise, is more readily able to ingest adequate ketone in order to provide a physiologically beneficial response without risk of physical discomfort (due to for instance ingestion of a large volume of liquid, or a bitter/otherwise aversive flavour). Administration of (R)-3-hydroxybutyl-(R)-3-hydroxybutyrate raises blood (R)-3-hydroxybutyrate concentrations higher, and for longer periods, than ketone salts such that a lower frequency of drinks is required to maintain elevated (R)-3-hydroxybutyrate levels. This also facilitates compliance of the subject with dosing regimens.

Administration of the compounds of the invention suppresses a subject's hunger and can therefore allow a subject to lose weight or prevent a subject from gaining weight (i.e. maintain a subject's weight). Advantageously, this reduces the risk of the subject developing a condition associated with being overweight, such as diabetes, cardiovascular disease, high blood pressure, or obesity.

The inventors have found that administration of the compounds of the invention not only reduces levels of the "hunger hormone" ghrelin, but also lowers circulating levels of glucagon-like peptide 1 (GLP-1) and of peptide tyrosine tyrosine (PYY) in a subject.

GLP-1 usually increases in the body after ingestion of food (see Example below) and stimulates the release of insulin to lower blood sugar levels. Similarly, PYY increases in the body after ingestion of food (see Example below). It is speculated, therefore, that the decrease in GLP-1 and PYY levels following administration of the compounds of the invention contributes to the suppression of hunger. That is, in some embodiments, the compounds and methods of the invention suppress hunger by controlling not only circulating ghrelin, but also GLP-1 and/or PYY levels. The compounds and methods of the invention have effects on ghrelin levels, GLP-1 levels and/or PYY levels in blood that work in tandem to suppress hunger and enable weight loss or weight maintenance.

In a preferred embodiment of the methods of the invention, plasma glucagon-like peptide 1 (GLP-1) levels are lowered. In another preferred embodiment of the methods of the invention, peptide tyrosine tyrosine (PYY) levels are lowered. Levels are lowered compared to baseline, i.e. levels just before administration of the compound of the invention. Typically, GLP-1 and/or PYY levels are lowered rapidly. For instance, GLP-1 and/or PYY levels are lowered within 30 minutes, typically within 15 minutes or preferably within 5 minutes of administration of a compound of the invention.

The GLP-1 and/or PYY level of the subject usually stays at a lower level that the initial level (i.e. the level at the time of administration of a compound of the invention) for at least one hour, preferably for at least two hours or up to five hours. These values assume that the subject is at rest and does not eat during the interval in question.

In a particularly preferred embodiment of the methods of the invention, both GLP-1 and PYY plasma levels are lowered.

Usually, in the methods of the invention, GLP-1 and/or PYY levels are lowered by 1 pg/ml or more. That is, the GLP-1 and/or PYY levels of the subject fall by at least 1 pg/ml compared to their respective levels in a subject shortly before (e.g. 1 minute before) administration of (R)-3-hydroxybutyrate and the precursors thereof described herein. In some embodiments of the methods of the invention, GLP-1 and/or PYY levels are lowered by 4 pg/ml or more, or 6 pg/ml or more. GLP-1 and/or PYY levels are typically lowered by up to 10 pg/ml in the methods of the invention.

Usually, the subject's GLP-1 level shortly before (e.g. 1 minute before) administration of said compounds is between 5 and 20 pg/ml. Thus, in some embodiments of the invention, the subject's plasma GLP-1 level is lowered from 12 pg/ml to 10 pg/ml or lower, preferably 8 pg/ml (e.g. 6 pg/ml) or lower.

Usually, the subject's PYY level shortly before (e.g. 1 minute before) administration of said compounds is between 40 and 80 pg/ml. Thus, in some embodiments of the invention, the subject's plasma PYY level is lowered from 65 pg/ml to 60 pg/ml or lower, preferably 55 pg/ml (e.g. 50 pg/ml) or lower.

Typically, the subject's GLP-1 and/or PYY levels remain at a level at least 1 pg/ml compared to the plasma GLP-1 and/or PYY level of the subject shortly before (e.g. 1 minute before) said compounds for up to five hours following administration of the compound. Of course, this period includes an initiation period (typically up to an hour, for example up to 30 minutes) during which the subject's GLP-1 and/or PYY levels are lowered by at least 1 pg/ml. For example, the subject's GLP-1 and/or PYY levels remain at a level at least 2 pg/ml or at least 5 pg/ml lower than the plasma GLP-1 and/or PYY levels shortly before administration during the period from 0.5 to 4 hours, e.g. from 1 to 3 hours, after administration.

Thus, in some embodiments of the methods of the invention the subject's GLP-1 level remains at 12 pg/ml or lower, preferably 8 pg/ml or 6 pg/ml or lower, during the period from 0.5 to 4 hours, e.g. from 1 to 3 hours, after administration.

In some embodiments of the methods of the invention the subject's PYY level remains at 70 pg/ml or lower, preferably 60 pg/ml or 50 pg/ml or lower, during the period from 0.5 to 4 hours, e.g. from 1 to 3 hours, after administration.

In particularly advantageous embodiments of the methods of the invention, the subject's GLP-1 and/or PYY levels are lowered by at least 2 pg/ml compared to the level shortly before administration, and remain at a value at least 2 pg/ml lower than the level shortly before administration for the period from 1 to 3 hours after administration.

Total ghrelin, GLP-1 and PYY from plasma can be measured using commercially available ELISA assays (for instance from Mercodia, Sweden and Merck Millipore, Germany).

In another embodiment of the methods of the invention, a subject's hunger is reduced from its baseline level for at least one hour, preferably for at least two hours, after administration of a compound of the invention.

In another embodiment of the methods of the invention, a subject's desire to eat is reduced from its baseline level for at least one hour, preferably for at least two hours, after administration of a compound of the invention.

The methods of the invention lead to an increase in levels of (R)-3-hydroxybutyrate (βHB) in the blood of a subject. It is the presence of βHB in the blood plasma that is believed to suppress hunger and hence to enable weight loss or prevent weight gain by lowering plasma ghrelin levels. It is also the presence of βHB in the blood that is believed to result in the lowering of GLP-1 and/or PYY plasma levels.

As has been noted above, the compounds and methods of the invention can rapidly raise the level of βHB in the blood plasma of a subject. This effect means that the compounds and methods of the invention can advantageously rapidly suppress hunger in a subject. This is particularly advantageous for the purposes of weight loss or prevention of weight gain. The compound of the invention may be consumed by a subject who is hungry to rapidly suppress the hunger. Therefore the time interval after consumption of the compound during which the subject is likely to over-eat as a result of perceived hunger is reduced, and hence the likelihood of over-eating is reduced.

In a preferred embodiment of the method of the invention, plasma levels of (R)-3-hydroxybutyrate in the subject are raised to 1 mM or more within 1 hour of consumption of the compound. For instance, plasma levels of (R)-3-hydroxybutyrate in the subject are usually raised to 1 mM or more within 30 minutes, preferably within 15 minutes or within 5 minutes of consumption of the compound.

In another preferred embodiment of the methods of the invention, the compound of the invention is consumed in response to a feeling of hunger in the subject.

The compounds and methods of the invention maintain an elevated level of βHB in the blood of a subject for a significant period of time. This means that the compounds and methods of the invention can maintain the suppression of hunger in a subject for a long time. Again, this is advantageous for the purposes of weight loss or prevention of weight gain as it increases the time during which the subject does not feel hungry and is therefore unlikely to over-eat.

In a preferred embodiment of the methods of the invention, plasma levels of (R)-3-hydroxybutyrate in the subject are 1 mM or more at least two hours after consumption of the compound of the invention. For instance, plasma levels of (R)-3-hydroxybutyrate in the subject are 1 mM or more at least three hours after consumption, or up to five hours after consumption of the compound of the invention.

In one embodiment, plasma levels of (R)-3-hydroxybutyrate in the subject are at least 1 mM for at least the period between 1 and 2 hours after consumption of the compound of the invention. For example, plasma levels of (R)-3-hydroxybutyrate in the subject are at least 1 mM for at least the period between 30 minutes and 3 hours after consumption of the compound of the invention.

In another embodiment of the methods of the invention, the maximum plasma level of (R)-3-hydroxybutyrate in the subject attained after consumption is at least 2 mM or at least 3 mM. Preferably, the plasma level of at least 2 mM or at least 3 mM of (R)-3-hydroxybutyrate is maintained for at least two hours, preferably at least three hours.

The compound of the invention is typically administered at least once a day. For example, the compound of the invention may be administered once, twice or three times a day.

Suitably, for a subject having a body mass index (BMI) of up to 25 kg/m$^2$, the compound is given at a level and regime such that the BMI is reduced by up to five kg/m$^2$, for instance such that the BMI is reduced by from 1 to 4 or from 2 to 3 kg/m$^2$. Where the subject has a BMI of 30 kg/m$^2$, the compound is given at a level and regime such that the BMI is reduced by up to 10 kg/m$^2$, for instance such that the BMI is reduced by from 2 to 8 or from 3 to 6 kg/m$^2$. Where the subject has a BMI of up to 40 kg/m$^2$, the compound is given at a level and regime such that the BMI is reduced by up to 15 kg/m$^2$, for instance such that the BMI is reduced by from 5 to 12 or from 7 to 10 kg/m$^2$. Where the subject has a BMI over 40 kg/m$^2$, the compound is given at a level and regime such that the BMI is reduced by up to 20 kg/m$^2$, for instance such that the BMI is reduced by from 10 to 18 kg/m$^2$.

In a further aspect the invention provides a method as defined in the first or second aspects of the invention comprising administering to the subject the compound or composition according to the invention for a period of 2 weeks wherein the BMI of the subject is reduced by at least 0.5 kg/m$^2$, preferably by at least 1 kg/m$^2$ and desirably by at least 2 kg/m$^2$. For instance, if the BMI of the subject starts out at 30 kg/m$^2$, the BMI after administration is 29.5 kg/m$^2$ or lower, preferably 29 kg/m$^2$ or lower, and desirably 28 kg/m$^2$ or lower. In preferred embodiments of this aspect, the method comprises administering an ester, or a compound or composition according to the third and fourth aspects of the invention.

Typically, the subject is overweight (e.g. obese).

Suitably the compound of the invention, preferably (R)-3-hydroxybutyrate-(R)-1,3-butanediol monoester, is ingested at a level of at least 100 mg per kilogram of body weight per day. Desirably, the ketone body or ketone body ester is ingested at a level adequate to provide a blood βHB level of at least 0.5 mM, preferably at least 1.0 mM, more preferably at least 2 mM and optimally at least 4 mM. Suitably the ketone body or ketone body ester is ingested at a level such that the blood plasma ketone level does not exceed 20 mM, suitably does not exceed 10 mM or 8 mM and may not exceed 5 mM.

The blood plasma level of ketone will depend on the body mass of the individual and we have found that oral consumption of (R)-3-hydroxybutyrate-(R)-1,3-butanediol monoester of at least 300 mg per kilogram of body weight provides a blood plasma concentration of (R)-3-hydroxybutyrate of around 1.5 mM and consumption at 500 mg/kg provides at least 3 mM (R)-3-hydroxybutyrate. At a dose of 1 g/kg of body weight of the subject, the blood (R)-3-hydroxybutyrate concentration is suitably at least 4 mM, preferably 5 mM. Upon oral consumption of monoester of 1.5 g/kg of body weight of the subject, the blood (R)-3-hydroxybutyrate concentration is suitably at least 7 mM, preferably at least 8 mM, especially at least 9 mM. A dosing regime comprises multiple drinks consumed separately.

Blood levels of (R)-3-hydroxybutyrate may be determined by commercially available testing kits, for example, (R)-3-hydroxybutyrate can be measured on whole blood using a handheld monitor and reagent strips (Precision Xtra, Abbott Diabetes Care, UK).

The compound and methods of the invention are suitable for treating subjects who have excess body weight whether they be overweight, obese or severely obese (that is a subject having a BMI respectively of 25 to 29.9 kg/m$^2$, a BMI of 30 to 39 kg/m$^2$ and a BMI of 40 kg/m$^2$ or above) to suppress hunger and desirably to reduce or maintain body weight. The compound and methods are suitable for treating subjects who have diabetes or pre-diabetes to suppress hunger and desirably to reduce or maintain body weight.

The cosmetic method of the invention is suitable for improving the bodily appearance of a human or animal to cause a cosmetically beneficial loss or maintenance of body weight where the subject is lean (that is, a subject having a BMI of under 25 kg/m$^2$).

In the method according to the first aspect of the invention, a compound of the invention may be used to treat a subject having a pre-diabetes, diabetes, metabolic syndrome, cardiovascular disease, high blood pressure, or a fatty liver disease including treating non-alcoholic fatty liver disease (NAFLD), non-alcoholic steatohepatitis (NASH), alcoholic steatohepatitis (ASH) and/or non-alcoholic fatty liver (NAFL).

Accordingly, one embodiment of the third aspect of the invention provides a compound selected from:
  (i) (R)-3-hydroxybutyrate;
  (ii) an ester of (R)-3-hydroxybutyrate; and
  (iii) an oligomer of (R)-3-hydroxybutyrate moieties;
or a pharmaceutically acceptable salt or solvate thereof; for use in treating or preventing cardiovascular disease, diabetes, pre-diabetes, high blood pressure non-alcoholic fatty liver disease (NAFLD), non-alcoholic steatohepatitis (NASH), alcoholic steatohepatitis (ASH) and non-alcoholic fatty liver (NAFL), wherein the compound is administered and hunger is suppressed, and plasma ghrelin levels are lowered.

Typically, a subject is overweight, obese or severely obese, for example where the subject has a BMI of 25 to 29.9 kg/m$^2$ (overweight), a BMI of 30 to 39.9 kg/m$^2$ (obese) and a BMI of 40 kg/m$^2$ or above (severely obese). The invention is particularly applicable to male subjects having a waist circumference of 94 cm (37 in) and to female subjects having a waist circumference of 80 cm (about 31.5 in) or more.

Compounds of the invention may be included with nutritional compositions and used in the cosmetic aspects of this invention. Suitably the nutritional composition comprises water and a source of (R)-3-hydroxybutyrate. Preferably, the composition comprises a source of (R)-3-hydroxybutyrate, (preferably an ester of (R)-3-hydroxybutyrate), a flavouring and optionally one or more of a protein, carbohydrate, sugars, fat, fibre, vitamins and minerals.

Suitably, the flavouring may comprise a fruit-based flavouring. In one embodiment, the flavouring is suitably bitter, for example coffee, chocolate, and cranberry. A bitter flavouring may be combined with other flavourings such as fruit based flavourings, for example grapefruit, raspberry and citrus.

The composition is suitably organoleptically acceptable. By "organoleptically acceptable" we mean that the composition must possess acceptable sensory properties of taste, colour, feel and odour.

The composition may comprise a mid-chain triglyceride (MCT). If present, the mid-chain triglyceride preferably comprises a mid-chain triglyceride having a formula $CH_2R_a$—$CH_2R_b$—$CH_2R_c$ wherein $R_a$, $R_b$ and $R_c$ are fatty acids having 5 to 12 carbon atoms. Suitably, $R_a$, $R_b$, and $R_c$ are fatty acids containing a six-carbon backbone (tri-C6:0) as tri-C6:0 MCTs are reported to be absorbed very rapidly by the gastrointestinal track.

Preferred compositions of the invention comprise salts (e.g. sodium and/or potassium salts) or glycerol esters, of (R)-3-hydroxybutyrate together with one or more mid-chain triglycerides.

The composition of the invention may comprise L-carnitine or a derivative of L-carnitine. Examples of derivatives of L-carnitine include decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine. Where a carnitine is employed, suitably the composition of the invention comprises i) a ketone body, preferably a ketone monoester, more preferably a (R)-3-hydroxybutyrate monoester and ii) L-carnitine or a derivative of L-carnitine and optionally an MCT.

Where MCT and L-carnitine or its derivative is employed, suitably the MCT is emulsified with the carnitine. Preferably 10 to 500 g of emulsified MCT is combined with 10 to 2000 mg of carnitine for example 50 g MCT (95% triC8:0) emulsified with 50 g of mono- and di-glycerides combined with 500 mg of L-carnitine. Preferably the level of the source of (R)-3-hydroxybutyrate is greater than the level of the MCT.

Compositions according to the invention may be provided in any suitable form, including a solid, for example a powder, tablet, bar, confectionery product or a granule, a liquid, for example a beverage, a gel, a capsule or any other conventional product form. The composition may be a food product, food supplement, dietary supplement, functional food or a nutraceutical or a component thereof.

Examples of food products into which the composition may be incorporated as an additive include snack bars, cereals, confectionery and probiotic formulations including yoghurts. Examples of beverages include soft beverages, alcoholic beverages, energy beverages, dry drink mixes, nutritional beverages and herbal teas for infusion or herbal blends for decoction in water.

A nutraceutical is a food ingredient, food supplement or food product, which is considered to provide a medical or health benefit, including the prevention and treatment of disease. In general, a nutraceutical is specifically adapted to confer a health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy.

The compound of the invention is typically formulated as a nutraceutical.

When in solid form, the composition suitably comprises at least 5% by weight of the compound of the invention, which is preferably an ester, more preferably at least 10% by weight and up to 95% by weight of the composition. Whilst a level of 15 to 30% by weight of a dry composition may be suitable, for example where the composition is a dry powder intended for use with a liquid to produce a liquid composition, a solid bar or product form suitably comprises from 30 to 95%, especially 50 to 95% by weight of the composition.

When the composition is in solid form the composition may further comprise one or more of the following components:
- a diluent for example lactose, dextrose, saccharose, cellulose, corn starch or potato starch;
- a lubricant for example silica, talc, stearic acid, magnesium or calcium stearate and/or polyethylene glycols;
- a binding agent for example starches, arabic gums, gelatin, methylcellulose, carboxymethylcellulose, or polyvinyl pyrrolidone;
- a disintegrating agent such as starch, alginic acid, alginates or sodium starch glycolate;
- an effervescing agent;
- a dyestuff;
- a flavouring;
- a wetting agent, for example lecithin, polysorbates, lauryl sulphates; and/or
- a carrier.

Where the composition is in liquid form, the composition suitably comprises a compound of the invention at a level of at least 1%, for example 3 to 40% by weight of the liquid composition, but may be higher for example up to 50% by weight of the composition depending on whether the composition is intended to be taken as a single dose or in multiple smaller doses to reach the desired blood ketone level.

The composition in liquid form may comprise several liquid components which are suitably blended together or may comprise liquid and solid components which are mixed with or dissolved in the liquid component as appropriate. In one embodiment, a dry composition comprising the ketone is diluted with a suitable liquid, for example water, fruit juice, yoghurt or milk, preferably at a ratio of 1:1 to 1:10, more preferably 1:3 to 1:7 of dry composition to liquid.

The composition may be provided, as desired, as a liquid product in a form ready for consumption or as a concentrate or paste suitable for dilution on use. The diluent for use with the liquid composition is preferably milk, fruit juice or water.

If desired, the composition may also be provided in encapsulated form, provided that the encapsulation material and the quantity in which it is used is suitable for safe human consumption.

One aspect of the invention provides compounds of the third aspect of the invention as defined above in a pharmaceutical composition, together with one or more pharmaceutically acceptable excipients.

Compounds of the invention may be present as pharmaceutically acceptable (or physiological) salts. As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the invention may be present as solvates. The term "solvate" refers to a complex or aggregate formed by one or more molecules of a solute, i.e. compounds of the invention or pharmaceutically-acceptable salts thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The compounds of the invention contain a chiral centre. Accordingly, they can be used in the form of a racemic mixture, an enantiomer, or a mixture enriched in one or more stereoisomer. The scope of the invention as described and claimed encompasses the racemic forms of the compounds of the invention as well as the individual enantiomers, and stereoisomer-enriched mixtures.

It will be appreciated that the term "or a pharmaceutically acceptable salt or solvate thereof" is intended to include all permutations of salts and solvates, such as solvates of physiologically-acceptable salts of compounds of the invention.

The pharmaceutical composition of the invention comprises a compound of the invention admixed with one or more pharmaceutically acceptable diluents, excipients or carriers.

Even though the compounds of the present invention (including their pharmaceutically acceptable salts, esters and pharmaceutically acceptable solvates) can be administered alone, they will generally be administered in admixture with a physiological carrier, excipient or diluent, particularly for humans. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Pharmaceutical compositions of the invention may comprise an adsorbent that is pharmaceutically acceptable. Suitably the adsorbent adsorbs the compound of the invention in or on the adsorbent. Advantageously, the flavour of the compound (which may be aversive to taste) is experienced to a lesser degree by the user than would be experienced on consumption of the same composition without the adsorbent. Preferably the adsorbent comprises a lattice or voids capable of retaining the compound of the invention. Any adsorbents used or known for use in food products may be employed. Examples of suitable adsorbents include a polymer hydrogel, for example a polymer of a crosslinked polycarboxylate homopolymer or copolymer, a clathrate, a cyclic oligosaccharide, for example cyclodextrins, and milk powder. The adsorbent may be present at any desired level according to the particular formulation and may be from 5% to 80% by weight of the composition, for example from 10 to 50%.

The invention provides in further aspect a kit comprising a compound in accordance with the third aspect of the invention, preferably an ester, or a composition according to the invention, and a ketone monitor and optionally instructions as to the level of product to consume per unit body weight to and a dosage regimen to suppress hunger, preferably to reduce or maintain body weight. Suitably, the user consumes the product and may then periodically test their blood plasma ketone level to determine whether further ingestion of ketone is required to reach or to maintain a desired blood plasma ketone level.

Typically, the subject of the invention is a mammal, for instance, a human.

Typically, use of the invention involves administering compounds orally or via a naso-gastric tube. Oral administration is preferred.

The present invention also provides a compound, as defined herein, in substantially pure form or in association with one or more pharmaceutically acceptable diluents or carriers for use in a method of suppressing hunger and optionally reducing or maintaining body weight in a subject.

As used herein, the term "substantially pure form" typically refers to a compound at a purity of 50% or greater, preferably 75% or greater, more preferably 90% or greater, even more preferably 95% or greater, and most preferably 99% or greater.

The following Example illustrates the invention.

Example

The invention is described by reference to the following a non-limiting example.

Study Design and Participants:

A randomised, single-blinded, cross-over study examined the effects of isocaloric ketone ester (KE) and dextrose drinks hunger in healthy, normal-weight participants (n=15) (FIG. 1A). An external Research Ethics Committee (14/LO/0288) approved the study, which was conducted at the University of Oxford in accordance with the Declaration of Helsinki. Participants were healthy, aged 21-42 and with no history of major illness (Anthropometric characteristics in Table 1). Participants provided written informed consent prior to inclusion. Drink order was randomised prior to commencement.

TABLE 1

Physical characteristics of subjects (n = 15)

| Characteristic | Mean (range) |
|---|---|
| Age (y) | 28 (21-42) |
| Height (m) | 1.8 (1.5-2.1) |
| Weight (kg) | 73 (54-111) |
| BMI (kg/m2) | 22 (19-28) |
| M/F | 10/5 |

Visit Protocol:

Participants refrained from alcohol and caffeine for 24 h prior to each visit and consumed an identical evening meal, at the same time before each visit. Testing started at 0800 h following an overnight (>8 h) fast, with a minimum of 72 h between visits. Venous blood samples (2 ml) were obtained using a 22G catheter inserted into an antecubital vein. Fasting blood samples were collected prior to all interventions and then at regular intervals for 4 h following the study drink. At identical time points, participants completed a validated three-measure visual-analogue-scale (VAS) to assess 'hunger,' 'desire to eat and' fullness' (Stubbs et aL, "The use of visual analogue scales to assess motivation to eat in human subjects: a review of their reliability and validity with an evaluation of new hand-held computerized systems for temporal tracking of hunger ratings", Br J Nutr, 2000, 84(4):405-15). Each drink contained 1.9 kCal/kg of βHB (as ketone ester) or dextrose. Drinks were diluted to 500 ml with a commercially available citrus-flavoured drink containing 65 kCal (5 g of carbohydrate) (Glaceau, UK). The dextrose drink was taste-matched using a bitterness additive (Symrise, Holzminden, Germany).

Analysis:

Blood βHB was measured using a handheld monitor and reagent strips (Precision Xtra, Abbott Diabetes Care, UK). Blood samples were stored on ice, centrifuged and duplicate plasma aliquots stored at −80° C. and analysed within 6 weeks. Plasma glucose was assayed using a commercial analyzer (ABX Pentra, France), whereas insulin, total ghrelin, GLP-1 and PYY were measured using commercially available ELISA assays (Mercodia, Sweden and Merck Millipore, Germany).

Statistical Methods:

Prism6™ software was used for statistical analysis. VAS scores were measured as a distance (mm), and normalised by taking the baseline distance for each visit as '0'. Values are means±SEM with significance at p<0.05. Following initial tests to ensure that normality and sphericity assumptions were not violated, two way repeated measures ANOVA or a Mann Whitney u-test with post-hoc correction were performed, as appropriate. Correlations were calculated using a two-tailed Pearson's test with a 95% confidence interval.

Figure 2C:
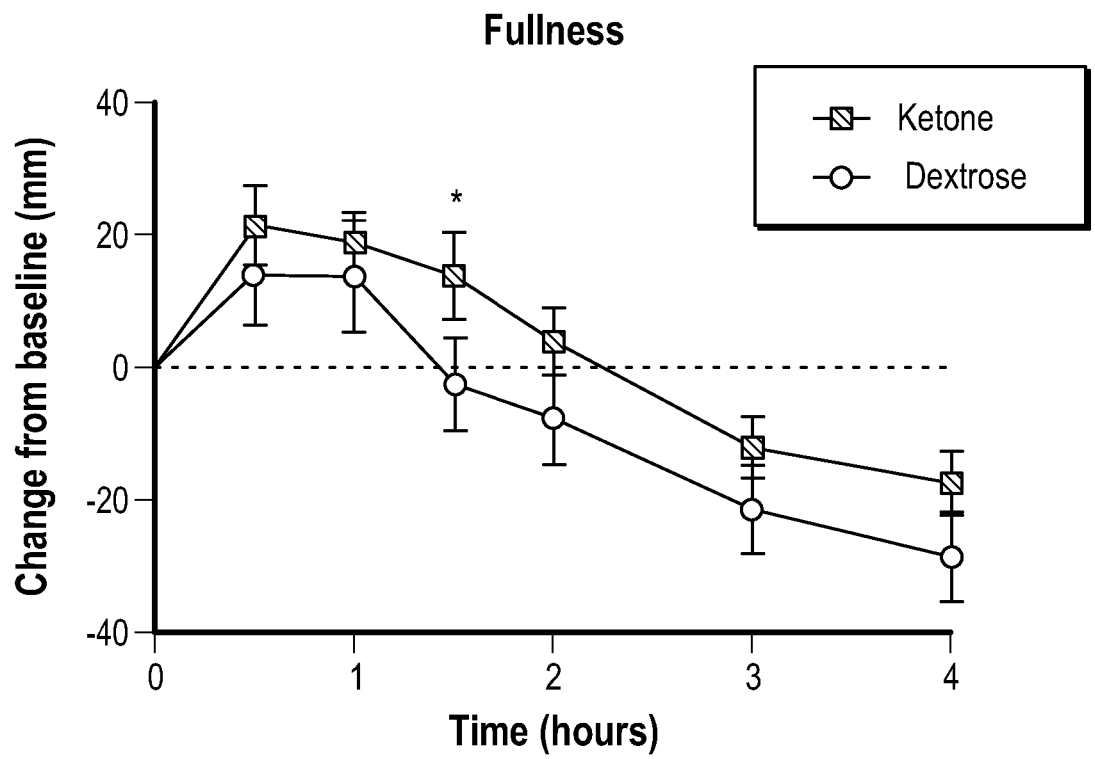
Figure 2D:
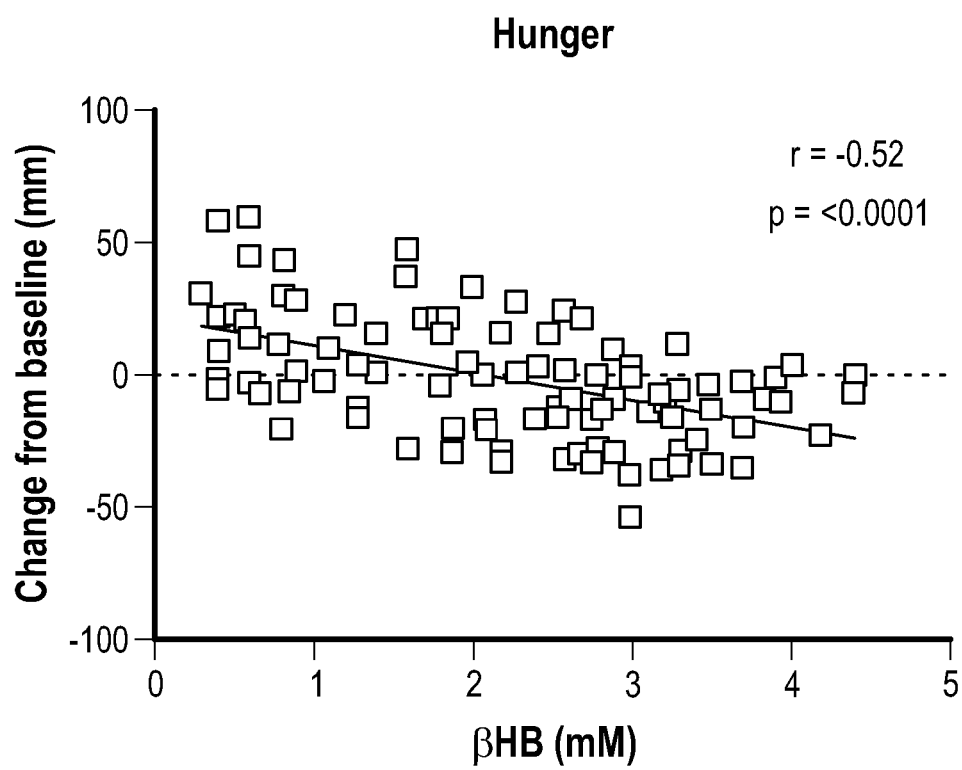
FIG. 2D-F shows significant negative correlations between blood $\beta$HB concentrations and both Hunger and Desire to eat, but not Fullness.
Figure 2E:
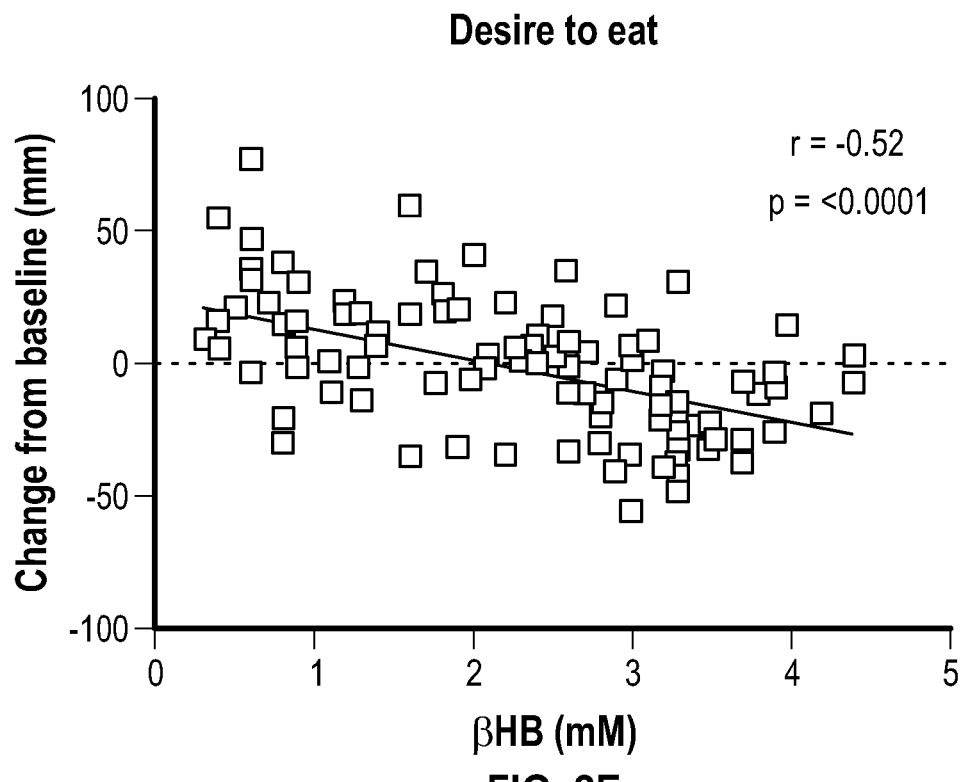
Figure 2F:
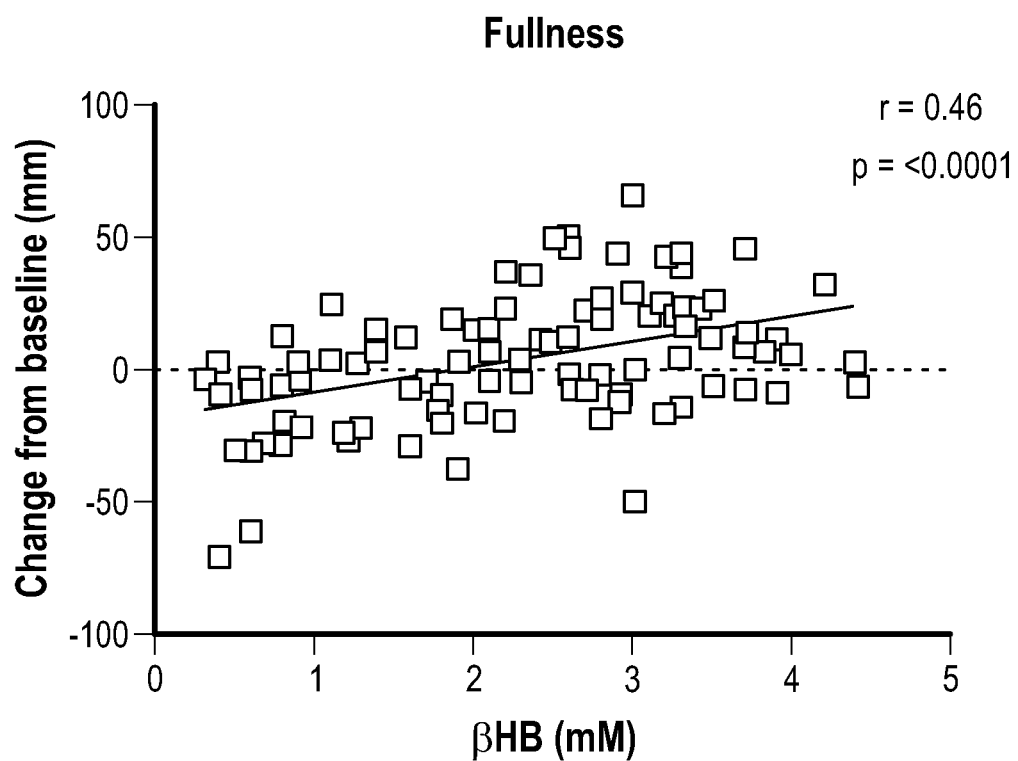

Results:

Following KE consumption, blood βHB levels rapidly increased to 3.3±0.2 mM after 1 h and gradually fell over the remaining 3 h whereas dextrose consumption had no effect on βHB levels (FIG. 1B). The perception of 'hunger' and 'desire to eat' fell by a similar extent after both drinks, but KE lowered both parameters by ~50% for 1.5 to 4 h compared to dextrose drinks (FIGS. 2A & B). Perceived 'Fullness' was the same following both dextrose and KE drinks. (FIG. 2C). Increasing ketonaemia was significantly correlated with decreased 'hunger' and 'desire to eat', and to increased 'fullness' (FIGS. 2D, E & F).

Figure 2G:
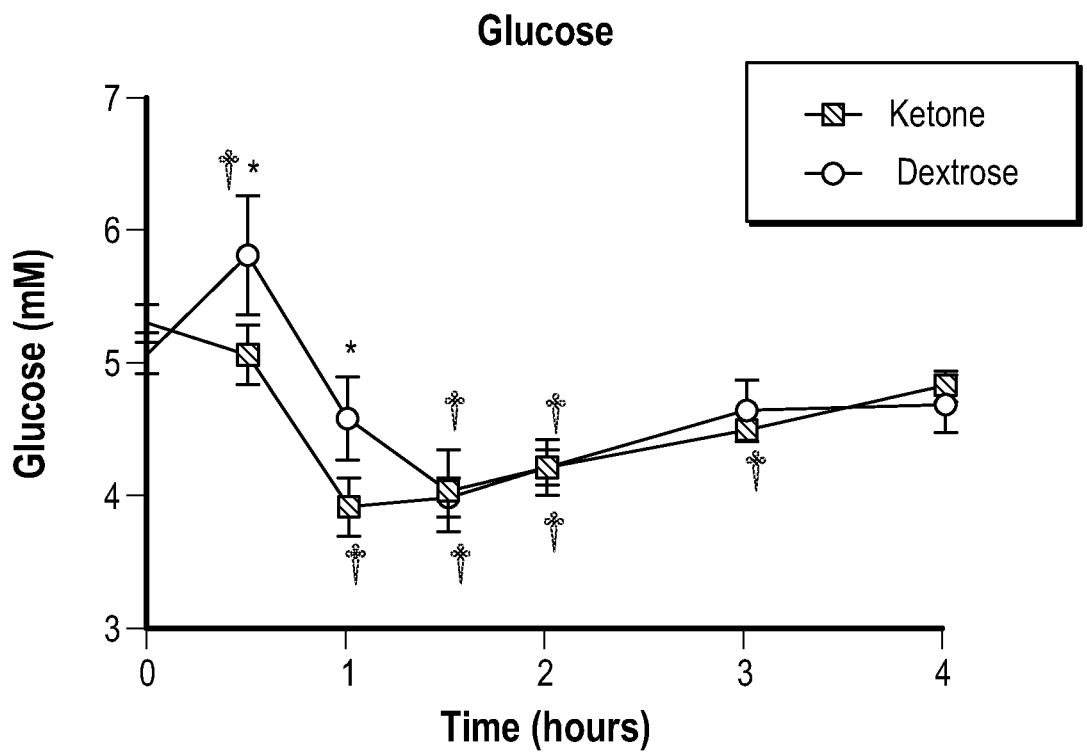
FIG. 2G-H shows that plasma concentrations of glucose and insulin were significantly higher following the dextrose drink.
Figure 2H:
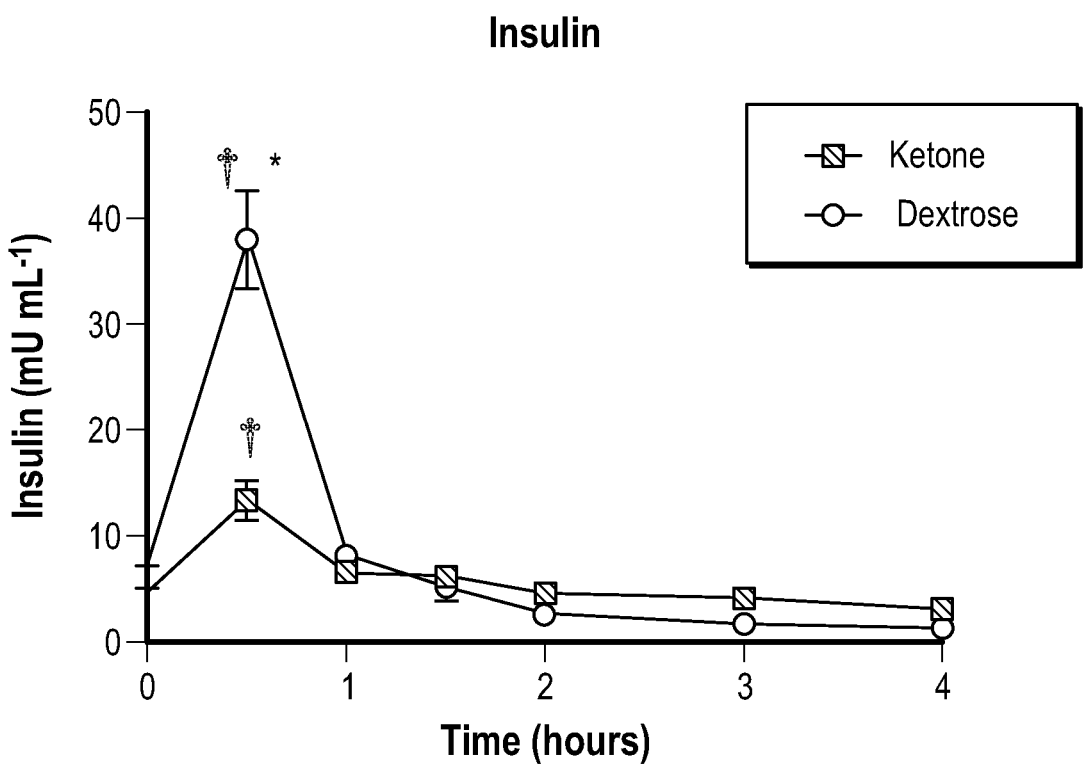
Figure 2I:
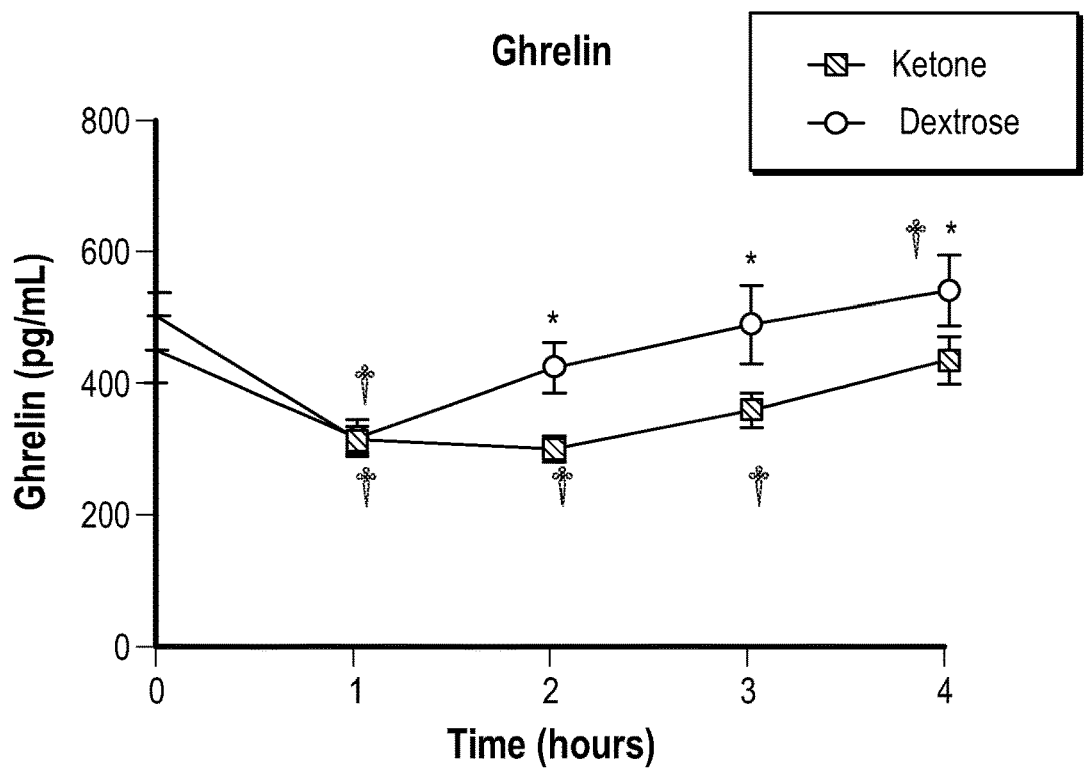
FIG. 2I-K shows that plasma concentrations of ghrelin, GLP-1 and PYY were significantly lower following the ketone drink compared with the dextrose drink.
Figure 2J:
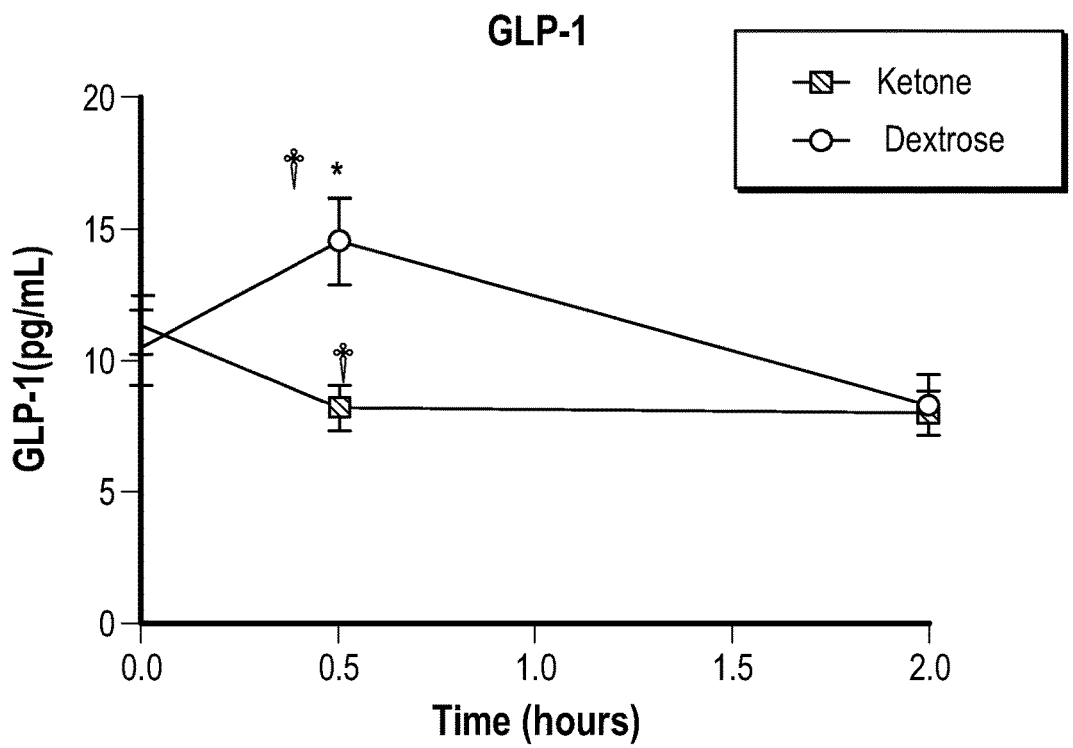
Figure 2K:
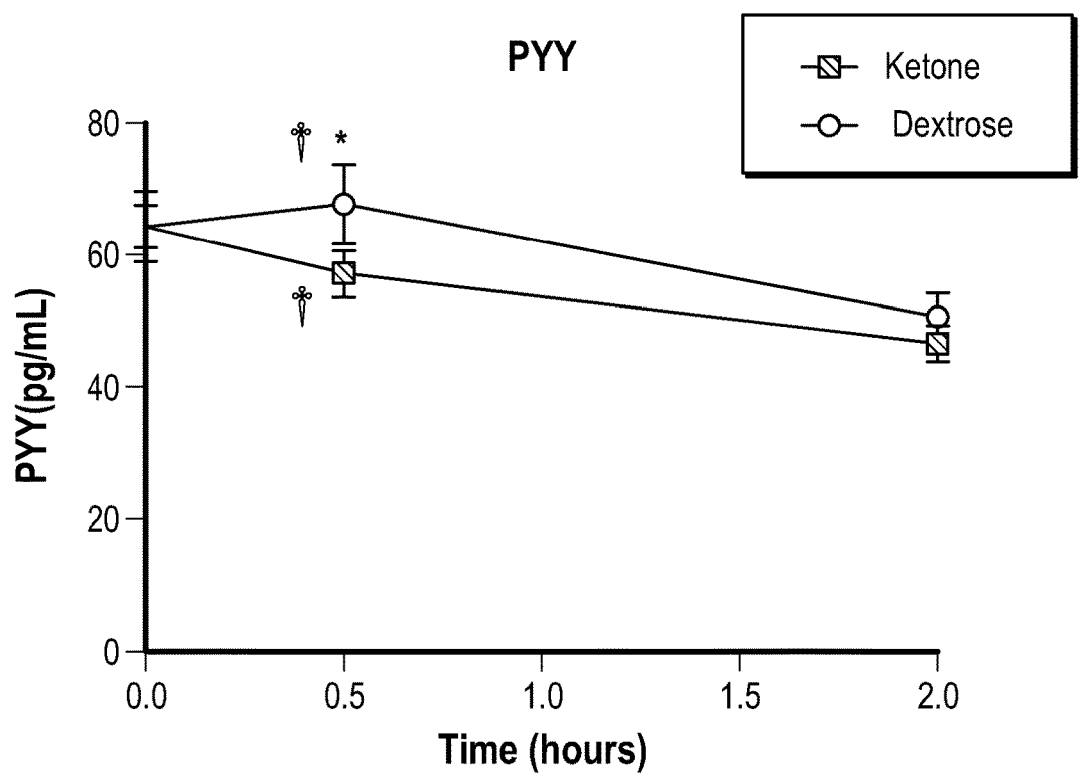
Figure 2L:
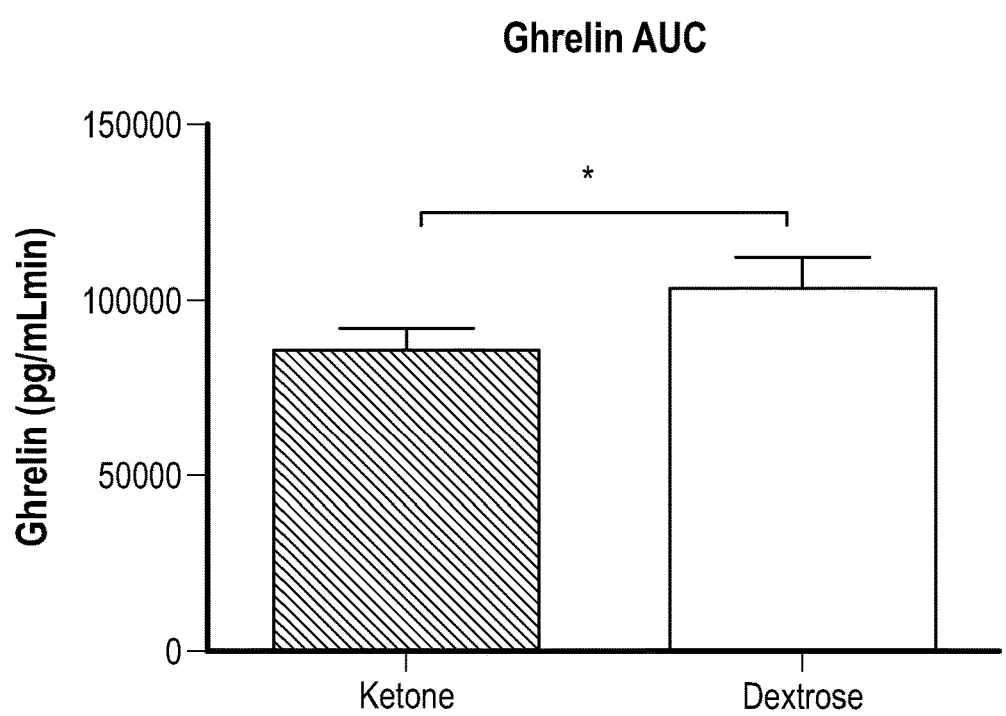
FIG. 2L shows that the plasma ghrelin total area under the curve (AUC) was significantly lower after the ketone drink than after the isocaloric dextrose drink. (* p<0.05: ketone vs. dextrose; t p<0.05 vs. baseline. Values are means±SEM.)

In order to explore possible mechanisms for these observations, plasma glucose, insulin, ghrelin, GLP-1 and PYY levels after KE and dextrose drinks were compared. Plasma glucose levels were significantly higher 30 min after dextrose than KE drinks (FIG. 2G) (5.8±0.5 mM vs. 5.1±0.2 mM, p=0.02). Plasma insulin levels rose after both KE and dextrose consumption, but levels were 3-fold higher 30 min after dextrose consumption compared to KE (38±5 mU/L vs. 13±2 mU/L, p<0.001) (FIG. 2H). After 90 min, there were no significant differences between plasma glucose and insulin levels following KE and dextrose drinks. However, plasma ghrelin fell to ≈320 pg/ml 1 h following both drinks, but the post-meal rise in ghrelin was significantly attenuated following KE consumption, remaining >100 pg/ml lower between 2-4 h post-drink than after dextrose. Total ghrelin AUC was 17% lower with KE vs. dextrose (86±6 ng/ml·min vs. 104±9 ng/ml·min, p<0.05) (FIGS. 2I & L). GLP-1 and PYY were elevated following dextrose consumption. However, plasma GLP-1 and PYY levels were altered by KE drinks after 30 min and were lower than dextrose (GLP-15 pg/ml vs. 8 pg/ml, p<0.001; PYY 68 pg/ml vs. 57 pg/ml, p=0.001) (FIGS. 2J & K).

DISCUSSION

It was found that KE drinks delayed the onset of 'hunger' and lowered the 'desire to eat,' in conjunction with a delayed rise in plasma ghrelin levels. Hunger suppression observed following KE drinks was not mediated by increased insulin, glucose, GLP-1 or PYY, which are conventionally believed to be signals that decrease hunger.

Hunger and satiety are signaled by two opposing neural pathways in the arcuate nucleus of the hypothalamus (Arc): neuropeptide Y (NPY)/agouti-related peptide neurons and pro-opiomelanocortin (POMC) neurons, respectively. Ghrelin, commonly known as 'the hunger hormone', activates orexigenic NPY neurons. NPY expressing neurons inhibit anorexigenic POMC neurons at both their site of origin in the Arc (via GABAnergic inhibition) and in the paraventricular nucleus of the hypothalamus by antagonism of $MC_4$ receptor activation. Damping the activity of NPY-expressing 'hunger' neurons by decreasing ghrelin levels may therefore be highly effective in reducing overall food intake.

The invention claimed is:

1. A method of suppressing hunger in a human or animal subject by lowering plasma ghrelin levels in the subject, comprising administration of a compound to the human or animal subject, wherein the compound comprises one or more of:
   (R)-3-hydroxybutyrate;
   (ii) an ester of (R)-3-hydroxybutyrate; or
   (iii) an oligomer of (R)-3-hydroxybutyrate moieties;
   or a pharmaceutically acceptable salt or solvate thereof, and
   wherein upon administration of the compound, plasma levels of (R)-3-hydroxybutyrate in the human or animal subject are 1 mM or more either within 1 hour of administration of the compound or at least two hours after administration of the compound.

2. A method according to claim 1 wherein the body weight of the human or animal subject is maintained or reduced.

3. A method according to claim 1 wherein the ester of (R)-3 hydroxybutyrate comprises a compound of Formula 1:

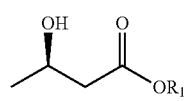

Formula 1 wherein in Formula 1:
   $R_1$ is a $C_1$-$C_6$ alkyl group, which alkyl group carries up to five —$OR_2$ substituents, wherein $R_2$ represents hydrogen, or a $C_1$-$C_6$ alkyl or wherein —$OR_2$ represents a (R)-3-hydroxybutyrate moiety; or
   $R_1$ is a moiety derived from an alcohol represented by $HOR_1$, wherein said alcohol is a sugar.

4. A method according to claim 3 wherein $R_1$ is a $C_1$-$C_6$ alkyl group substituted with 1, 2 or 3 —$OR_2$ substituents.

5. A method according to claim 3 wherein $R_2$ is H.

6. A method according to claim 3, wherein $R_1$ comprises —$CH_2$—$CH(OH)$—$CH_2(OH)$ or —$CH_2$—$CH_2$—$CH(OH)$—$CH_3$.

7. A method according to claim 3 wherein $R_1$ is a moiety derived from an alcohol represented by $HOR_1$, wherein said alcohol comprises a sugar selected from altrose, arabinose, dextrose, erythrose, fructose, galactose, glucose, gulose, idose, lactose, lyxose, mannose, ribose, ribulose, sucrose, talose, threose, and xylose.

8. A method according to claim 1 wherein the oligomer comprises a compound of Formula 2:

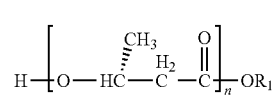

Formula 2 wherein $R_1$ is selected from:
   a $C_1$-$C_6$ alkyl group substituted with 1, 2 or 3 —$OR_2$ substituents, wherein $R_2$ represents hydrogen, or a $C_1$-$C_6$ alkyl, or wherein —$OR_2$ represents a (R)-3-hydroxybutyrate moiety;
   —$CH_2$—$CH(OH)$—$CH_2(OH)$ or —$CH_2$—$CH_2$—$CH(OH)$—$CH_3$; or
   a moiety derived from an alcohol of formula $HOR_1$, wherein said alcohol comprises a sugar selected from altrose, arabinose, dextrose, erythrose, fructose, galactose, glucose, gulose, idose, lactose, lyxose, mannose, ribose, ribulose, sucrose, talose, threose, and xylose; and
   n is an integer of from 2 to 100.

9. A method according to claim 1 wherein the compound comprises (R)-3-hydroxybutyrate (R)-1,3-butanediol monoester of Formula 3:

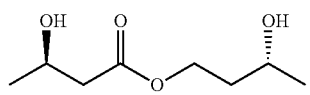

Formula 3

10. A method according to claim 1 wherein hunger is suppressed by lowering of plasma glucagon-like peptide 1 levels and/or by lowering of peptide tyrosine tyrosine levels.

11. A method according to claim 1 wherein the compound is administered to the human or animal subject at least once a day, and/or the compound is administered to the human or animal subject from 0 to 30 minutes before a meal.

12. A method of suppressing hunger in a human or animal subject by lowering plasma ghrelin levels in the subject, comprising administration of a compound to the human or animal subject, wherein the compound comprises one or more of:
   (R)-3-hydroxybutyrate;
   (ii) an ester of (R)-3-hydroxybutyrate; or
   (iii) an oligomer of (R)-3-hydroxybutyrate moieties;
   or a pharmaceutically acceptable salt or solvate thereof, wherein the compound is administered in response to a feeling of hunger in the human or animal subject.

13. A method of suppressing hunger in a human or animal subject by lowering plasma ghrelin levels in the subject, comprising administration of a compound to the human or animal subject, wherein the compound comprises one or more of:
   (R)-3-hydroxybutyrate;
   (ii) an ester of (R)-3-hydroxybutyrate; or
   (iii) an oligomer of (R)-3-hydroxybutyrate moieties;
   or a pharmaceutically acceptable salt or solvate thereof, wherein the human or animal subject is overweight (having a BMI in the range 25 to less than 30 $k/m^2$), obese (having a BMI in the range 30 to less than 40 k/m²) or severely obese (having a BMI of 40 k/m² or above).

14. A method according to claim 1 wherein the human or animal subject is pre-diabetic or diabetic, and/or the human subject is unwilling or unable to follow a ketogenic diet.

15. A method according to claim 12 wherein the body weight of the human or animal subject is maintained or reduced.

16. A method according to claim 12 wherein the ester of (R)-3 hydroxybutyrate comprises a compound of Formula 1, and/or the oligomer comprises a compound of Formula 2:

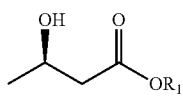

Formula 1 wherein in Formula 1:
   $R_1$ is a $C_1$-$C_6$ alkyl group, which alkyl group carries up to five —$OR_2$ substituents, wherein $R_2$ represents hydrogen, or a $C_1$-$C_6$ alkyl or wherein —$OR_2$ represents a (R)-3-hydroxybutyrate moiety; or
   $R_1$ is a moiety derived from an alcohol represented by $HOR_1$, wherein said alcohol is a sugar;

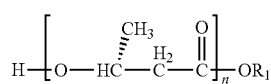

Formula 2 wherein in Formula 2, $R_1$ is selected from:
   a $C_1$-$C_6$ alkyl group substituted with 1, 2 or 3—$OR_2$ substituents, wherein $R_2$ represents hydrogen, or a $C_1$-$C_6$ alkyl, or wherein —$OR_2$ represents a (R)-3-hydroxybutyrate moiety;
   —$CH_2$—$CH(OH)$—$CH_2(OH)$ or —$CH_2$—$CH_2$—$CH(OH)$—$CH_3$; or
   a moiety derived from an alcohol of formula $HOR_1$, wherein said alcohol comprises a sugar selected from altrose, arabinose, dextrose, erythrose, fructose, galactose, glucose, gulose, idose, lactose, lyxose, mannose, ribose, ribulose, sucrose, talose, threose, and xylose; and
   n is an integer of from 2 to 100.

17. A method according to claim 12 wherein the compound comprises (R)-3-hydroxybutyrate (R)-1,3-butanediol monoester of Formula 3:

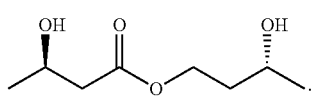

Formula 3

18. A method according to claim 12 wherein hunger is suppressed by lowering plasma glucagon-like peptide 1 levels and/or by lowering peptide tyrosine tyrosine levels.

19. A method according to claim 12 wherein plasma levels of (R)-3-hydroxybutyrate in the human or animal subject are raised to 1 mM or more either within 1 hour of administration of the compound or at least two hours after administration of the compound.

20. A method according to claim 12 wherein the compound is administered to the human or animal subject at least once a day, and/or the compound is administered to the human or animal subject from 0 to 30 minutes before a meal.

21. A method according to claim 12 wherein the human or animal subject is overweight (having a BMI in the range 25 to less than 30 k/m²), obese (having a BMI in the range 30 to less than 40 k/m²) or severely obese (having a BMI of 40 k/m² or above).

22. A method according to claim 12 wherein the human or animal subject is pre-diabetic or diabetic, and/or the human subject is unwilling or unable to follow a ketogenic diet.

23. A method according to claim 13 wherein the body weight of the human or animal subject is maintained or reduced.

24. A method according to claim 13 wherein the ester of (R)-3 hydroxybutyrate comprises a compound of Formula 1, and/or the oligomer comprises a compound of Formula 2:

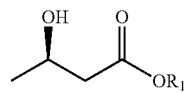

Formula 1 wherein in Formula 1:
   $R_1$ is a $C_1$-$C_6$ alkyl group, which alkyl group carries up to five —$OR_2$ substituents, wherein $R_2$ represents hydrogen, or a $C_1$-$C_6$ alkyl or wherein —$OR_2$ represents a (R)-3-hydroxybutyrate moiety; or
   $R_1$ is a moiety derived from an alcohol represented by $HOR_1$, wherein said alcohol is a sugar;

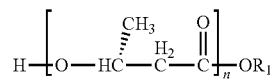

Formula 2 wherein in Formula 2, $R_1$ is selected from:
   a $C_1$-$C_6$ alkyl group substituted with 1, 2 or 3—$OR_2$ substituents, wherein $R_2$ represents hydrogen, or a $C_1$-$C_6$ alkyl, or wherein —$OR_2$ represents a (R)-3-hydroxybutyrate moiety;
   —$CH_2$—$CH(OH)$—$CH_2(OH)$ or —$CH_2$—$CH_2$—$CH(OH)$—$CH_3$; or
   a moiety derived from an alcohol of formula $HOR_1$, wherein said alcohol comprises a sugar selected from altrose, arabinose, dextrose, erythrose, fructose, galactose, glucose, gulose, idose, lactose, lyxose, mannose, ribose, ribulose, sucrose, talose, threose, and xylose; and
   n is an integer of from 2 to 100.

25. A method according to claim 13 wherein the compound comprises (R)-3-hydroxybutyrate (R)-1,3-butanediol monoester of Formula 3:

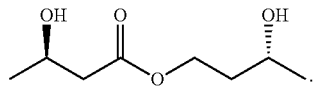

Formula 3

26. A method according to claim 13 wherein hunger is suppressed by lowering plasma glucagon-like peptide 1 levels and/or by lowering peptide tyrosine tyrosine levels.

27. A method according to claim 13 wherein plasma levels of (R)-3-hydroxybutyrate in the human or animal subject are raised to 1 mM or more either within 1 hour of administration of the compound or at least two hours after administration of the compound.

28. A method according to claim 13 wherein the compound is administered to the human or animal subject at least once a day, and/or the compound is administered to the human or animal subject from 0 to 30 minutes before a meal.

29. A method according to claim 13 wherein the compound is administered in response to a feeling of hunger in the human or animal subject.

30. A method according to claim 13 wherein the human or animal subject is pre-diabetic or diabetic, and/or the human subject is unwilling or unable to follow a ketogenic diet.

* * * * *